US009162015B2

(12) United States Patent
Johnson et al.

(10) Patent No.: US 9,162,015 B2
(45) Date of Patent: *Oct. 20, 2015

(54) SYSTEM FOR PERCUTANEOUSLY ADMINISTERING REDUCED PRESSURE TREATMENT USING BALLOON DISSECTION

(71) Applicant: KCI Licensing, Inc., San Antonio, TX (US)

(72) Inventors: Royce W. Johnson, Universal City, TX (US); Larry D. Swain, San Antonio, TX (US); Douglas A. Cornet, San Antonio, TX (US); Michael Manwaring, San Antonio, TX (US); Jonathan Kagan, Hopkins, MN (US)

(73) Assignee: KCI Licensing, Inc., San Antonio, TX (US)

( * ) Notice: Subject to any disclaimer, the term of this patent is extended or adjusted under 35 U.S.C. 154(b) by 105 days.

This patent is subject to a terminal disclaimer.

(21) Appl. No.: 14/088,192

(22) Filed: Nov. 22, 2013

(65) Prior Publication Data

US 2014/0081246 A1 Mar. 20, 2014

Related U.S. Application Data

(60) Division of application No. 13/241,044, filed on Sep. 22, 2011, now Pat. No. 8,617,140, which is a continuation of application No. 11/717,892, filed on Mar. 13, 2007, now Pat. No. 8,029,498.

(60) Provisional application No. 60/782,171, filed on Mar. 14, 2006.

(51) Int. Cl.
*A61M 25/00* (2006.01)
*A61M 25/10* (2013.01)
(Continued)

(52) U.S. Cl.
CPC .............. *A61M 1/0084* (2013.01); *A61B 17/88* (2013.01); *A61F 2/0077* (2013.01);
(Continued)

(58) Field of Classification Search
CPC ........... A61F 2/30767; A61F 13/00068; A61F 2002/3068; A61F 2002/30677; A61M 37/00; A61M 2025/0057; A61M 2025/1086; A61B 17/12168; A61B 17/12181; A61B 17/12186; A61B 17/1219; A61B 17/12195
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
(Continued)

*Primary Examiner* — Adam Marcetich

(57) ABSTRACT

A reduced pressure delivery system for applying reduced pressure tissue treatment to a tissue site is provided. The system includes a manifold delivery tube and a balloon having an inner space. The balloon is capable of assuming collapsed and expanded positions. The system further includes a manifold having a plurality of flow channels. The manifold is disposed within the inner space of the balloon. A sharp tip is configured to be delivered within the manifold delivery tube to puncture the balloon.

20 Claims, 20 Drawing Sheets

(51) Int. Cl.

| | |
|---|---|
| *A61M 1/00* | (2006.01) |
| *A61B 17/88* | (2006.01) |
| *A61M 27/00* | (2006.01) |
| *A61M 37/00* | (2006.01) |
| *A61F 2/00* | (2006.01) |
| *A61L 31/14* | (2006.01) |
| *A61M 5/14* | (2006.01) |
| *A61F 13/02* | (2006.01) |
| *A61F 13/00* | (2006.01) |
| *A61F 2/30* | (2006.01) |
| *A61B 17/12* | (2006.01) |
| *A61B 17/135* | (2006.01) |
| *A61B 17/80* | (2006.01) |
| *A61F 2/36* | (2006.01) |

(52) U.S. Cl.
 CPC ............ *A61F 2/3662* (2013.01); *A61L 31/146* (2013.01); *A61M 1/0088* (2013.01); *A61M 1/0092* (2014.02); *A61M 5/14* (2013.01); *A61M 27/00* (2013.01); *A61M 37/00* (2013.01); *A61B 17/1219* (2013.01); *A61B 17/12168* (2013.01); *A61B 17/12181* (2013.01); *A61B 17/12186* (2013.01); *A61B 17/12195* (2013.01); *A61B 17/1355* (2013.01); *A61B 17/80* (2013.01); *A61F 2/30767* (2013.01); *A61F 2/36* (2013.01); *A61F 13/00068* (2013.01); *A61F 13/0216* (2013.01); *A61F 2002/0086* (2013.01); *A61F 2002/3068* (2013.01); *A61F 2002/30677* (2013.01); *A61F 2002/30785* (2013.01); *A61F 2002/30787* (2013.01); *A61F 2002/30968* (2013.01); *A61F 2002/368* (2013.01); *A61F 2002/3611* (2013.01); *A61F 2002/3625* (2013.01); *A61F 2002/3694* (2013.01); *A61F 2310/00395* (2013.01); *A61F 2310/00592* (2013.01); *A61F 2310/00928* (2013.01); *A61M 1/0023* (2013.01); *A61M 1/0037* (2013.01); *A61M 2025/1086* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,188,630 A * | 2/1993 | Christoudias | 606/1 |
| 5,215,522 A | 6/1993 | Page et al. | |
| 5,232,444 A * | 8/1993 | Just et al. | 604/110 |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,374,261 A * | 12/1994 | Yoon | 604/385.01 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,649,902 A * | 7/1997 | Yoon | 604/1 |
| 5,827,224 A * | 10/1998 | Shippert | 604/73 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,398,758 B1 * | 6/2002 | Jacobsen et al. | 604/104 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,029,498 B2 * | 10/2011 | Johnson et al. | 604/543 |
| 2001/0004710 A1 * | 6/2001 | Felt et al. | 623/17.12 |
| 2002/0026182 A1 * | 2/2002 | Joye et al. | 606/21 |
| 2002/0077661 A1 | 6/2002 | Saadat | |
| 2002/0115951 A1 | 8/2002 | Norstrem et al. | |

(56) References Cited

U.S. PATENT DOCUMENTS

| | | | |
|---|---|---|---|
| 2002/0120185 | A1 | 8/2002 | Johnson |
| 2002/0143286 | A1 | 10/2002 | Tumey |
| 2005/0043678 | A1* | 2/2005 | Freyman et al. ......... 604/103.01 |
| 2006/0079852 | A1 | 4/2006 | Bubb et al. |
| 2006/0149309 | A1* | 7/2006 | Paul et al. .................... 606/195 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 01-094836 | 4/1989 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 99-27862 A1 | 6/1999 |
| WO | 2005074814 A2 | 8/2005 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 pages English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

* cited by examiner

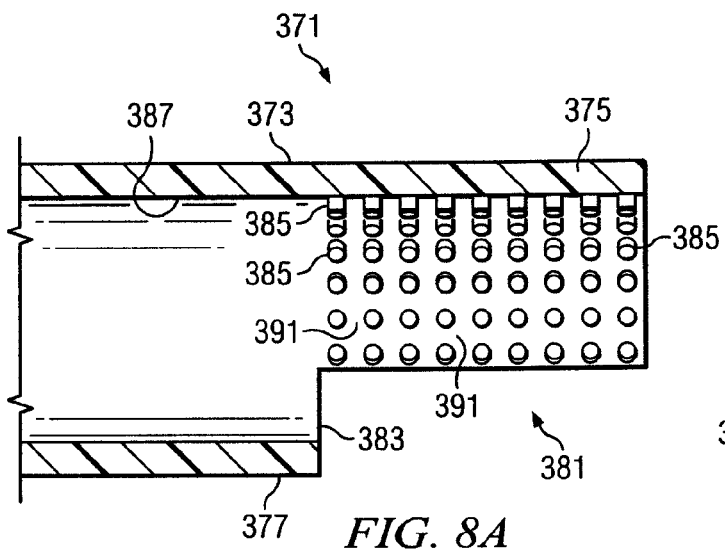
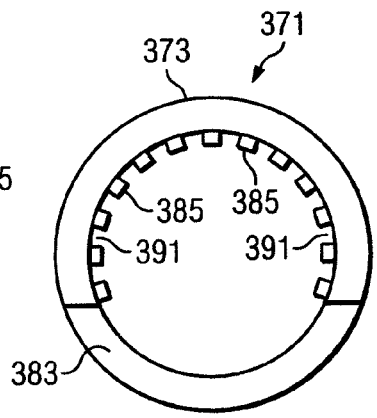
*FIG. 8A*
*FIG. 8B*
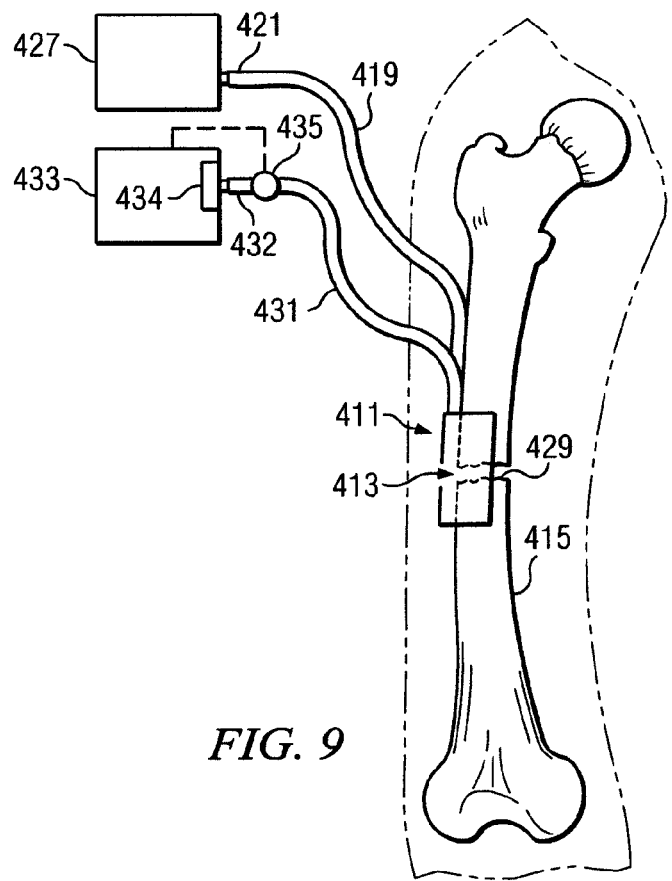
*FIG. 9*

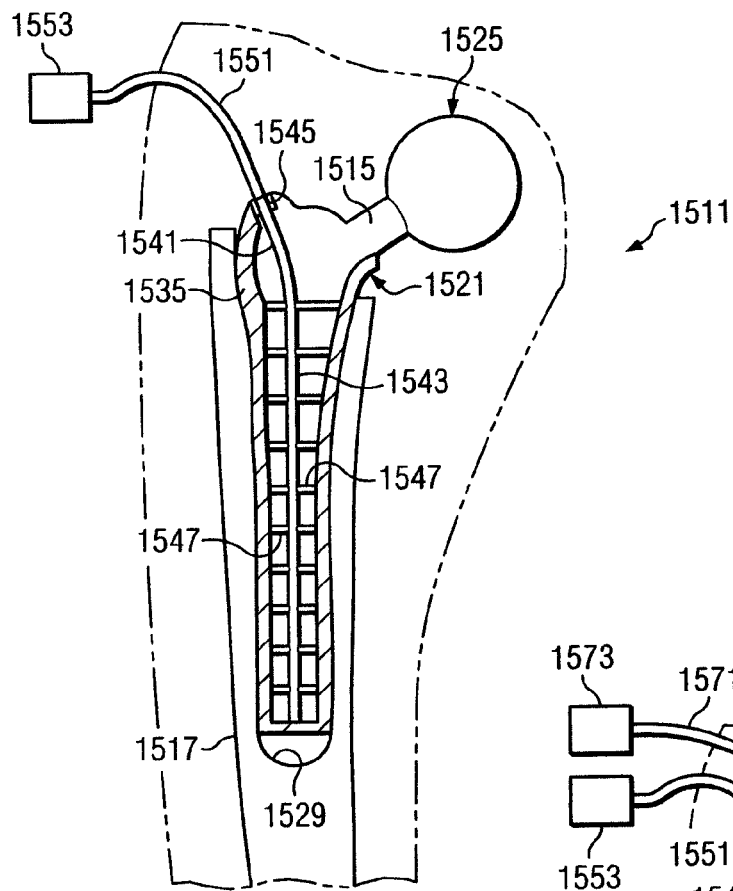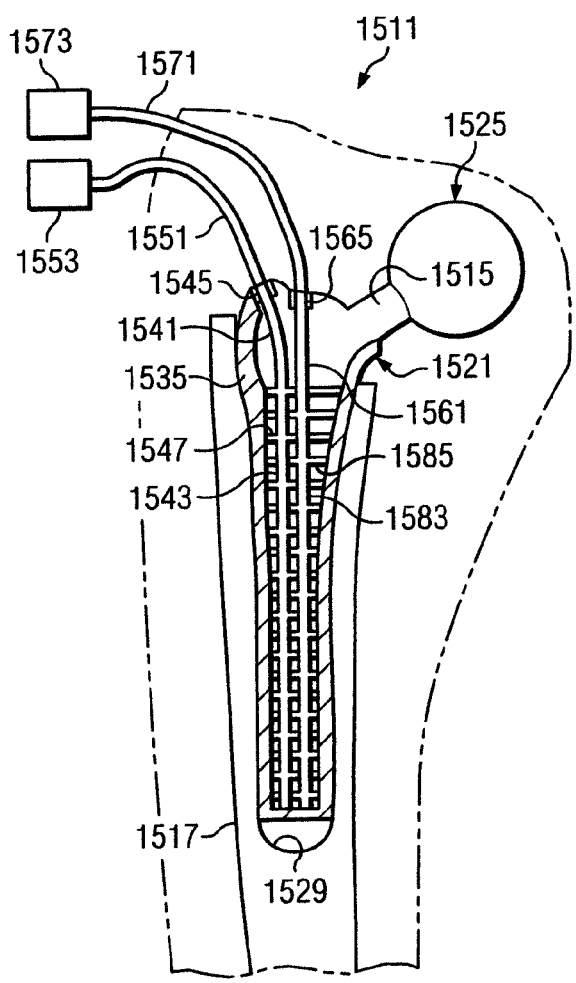
FIG. 32
FIG. 33

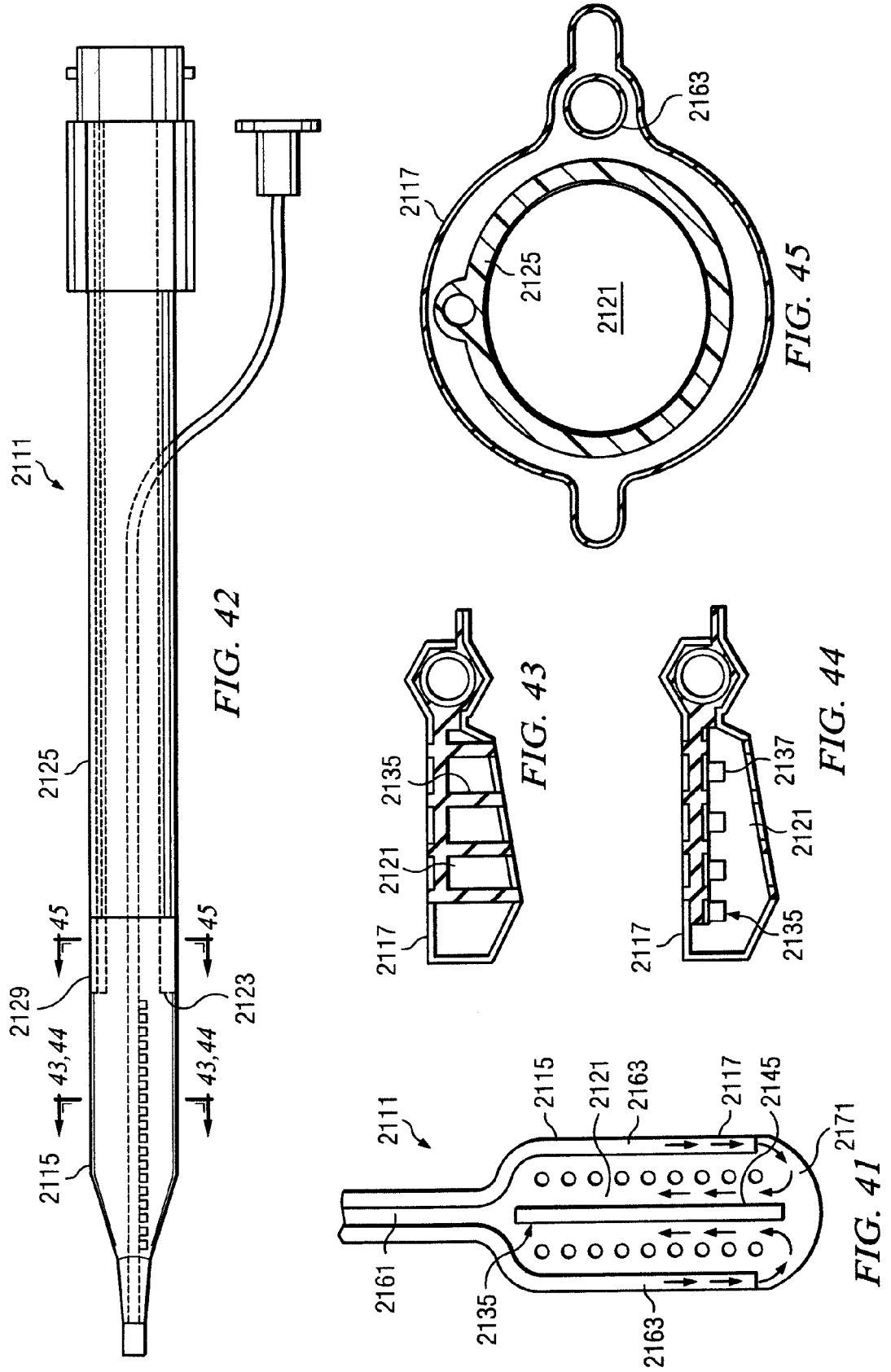

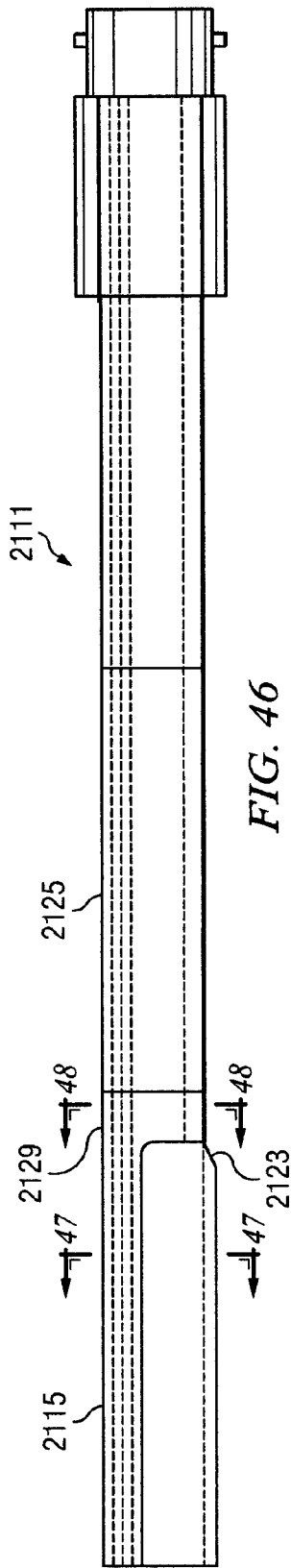
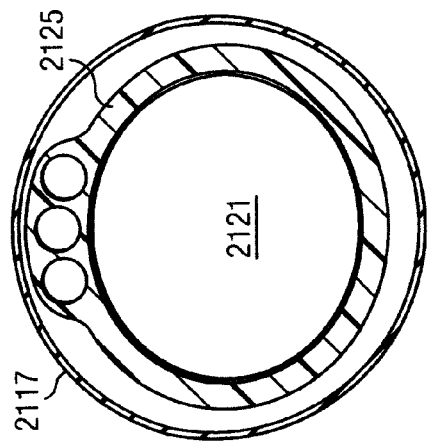
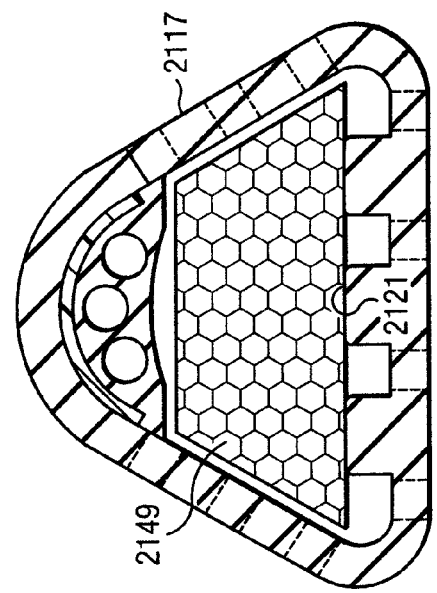
FIG. 46
FIG. 47
FIG. 48

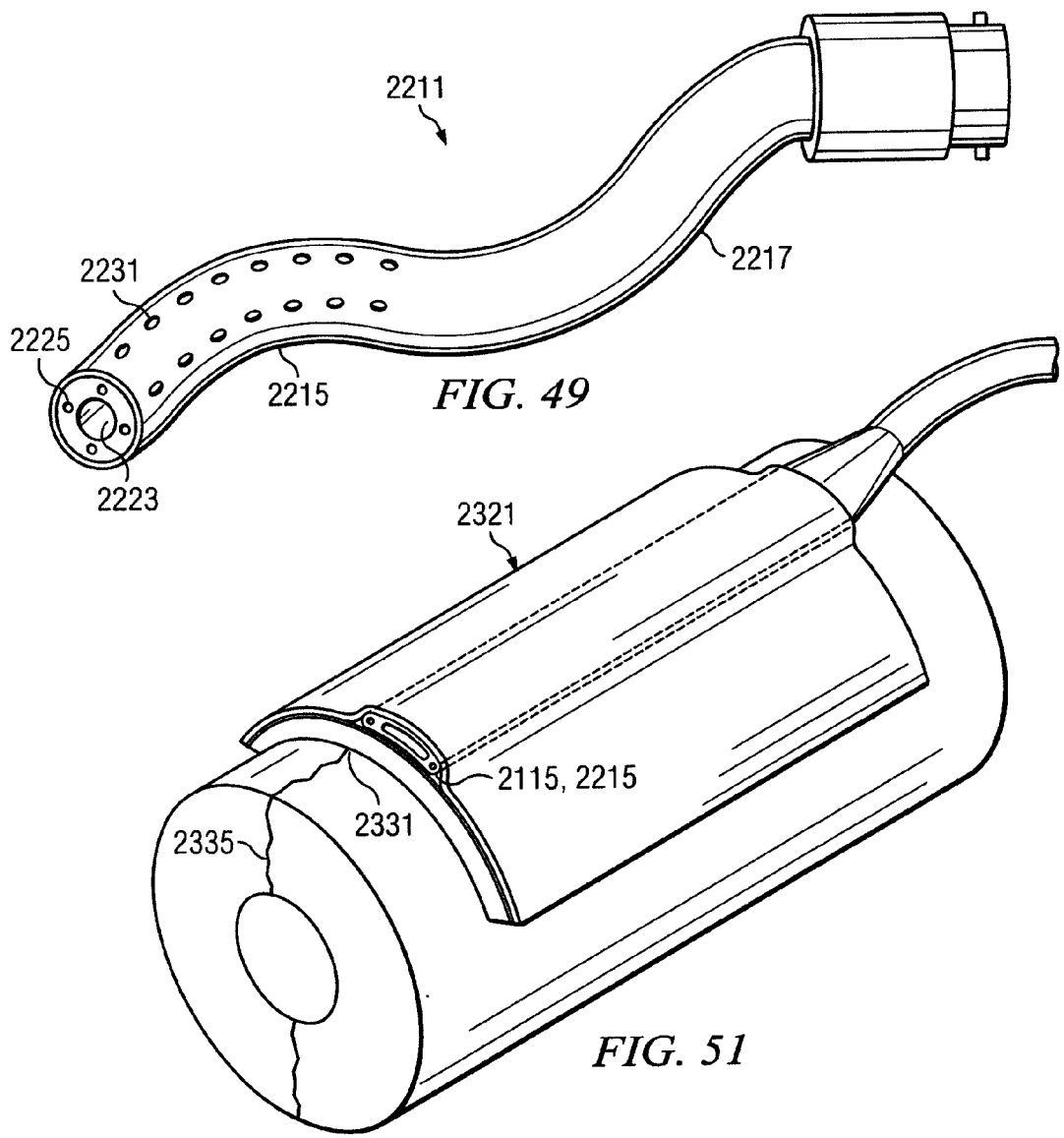
FIG. 49
FIG. 51
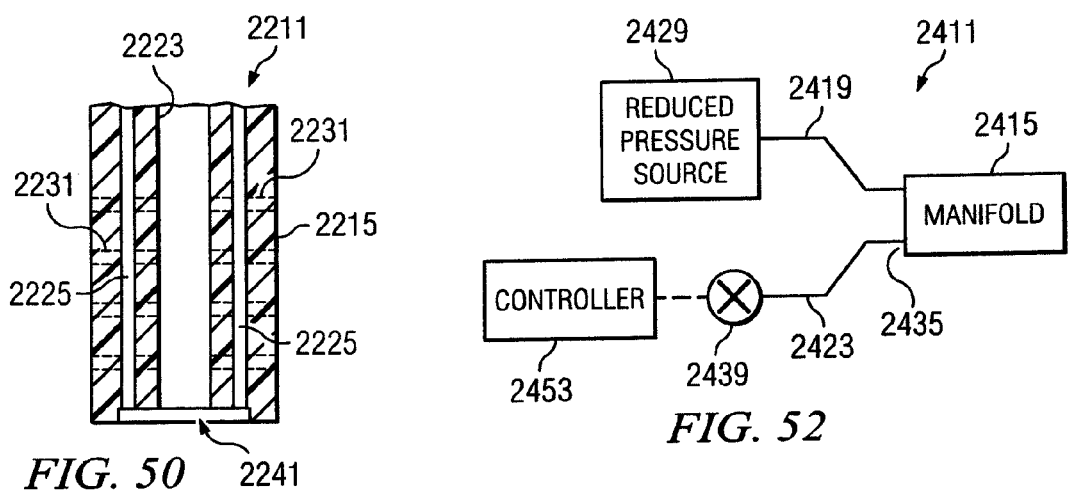
FIG. 50
FIG. 52

SYSTEM FOR PERCUTANEOUSLY ADMINISTERING REDUCED PRESSURE TREATMENT USING BALLOON DISSECTION

CROSS REFERENCE TO RELATED APPLICATIONS

This application is a divisional of U.S. patent application Ser. No. 13/241,044, filed Sep. 22, 2011, which is a continuation of U.S. patent application Ser. No. 11/717,892, filed Mar. 13, 2007, which issued as U.S. Pat. No. 8,029,498 on Oct. 4, 2011, which claims the benefit of U.S. Provisional Application No. 60/782,171, filed Mar. 14, 2006, all of which are hereby incorporated by reference.

BACKGROUND OF THE INVENTION

1. Field of the Invention

This invention relates generally to a system or method of promoting tissue growth and more specifically a system for applying reduced pressure tissue treatment to a tissue site.

2. Description of Related Art

Reduced pressure therapy is increasingly used to promote wound healing in soft tissue wounds that are slow to heal or non-healing without reduced pressure therapy. Typically, reduced pressure is applied to the wound site through an open-cell foam that serves as a manifold to distribute the reduced pressure. The open-cell foam is sized to fit the existing wound, placed into contact with the wound, and then periodically replaced with smaller pieces of foam as the wound begins to heal and become smaller. Frequent replacement of the open-cell foam is necessary to minimize the amount of tissue that grows into the cells of the foam. Significant tissue in-growth can cause pain to patients during removal of the foam.

Reduced pressure therapy is typically applied to non-healing, open wounds. In some cases, the tissues being healed are subcutaneous, and in other cases, the tissues are, located within or on dermal tissue. Traditionally, reduced pressure therapy has primarily been applied to soft tissues. Reduced pressure therapy has not typically been used to treat closed, deep-tissue wounds because of the difficulty of access presented by such wounds. Additionally, reduced pressure therapy has not been used in connection with healing bone defects or promoting bone growth, primarily due to access problems. Surgically exposing a bone to apply reduced pressure therapy may create more problems than it solves. Finally, devices and systems for applying reduced pressure therapy have advanced little beyond the open-cell foam pieces that are manually shaped to fit a wound site and then removed following a period of reduced pressure therapy.

SUMMARY

The problems presented by existing wound-healing system and methods are solved by the systems and methods of the present invention. In one embodiment, a reduced pressure delivery system for applying reduced pressure tissue treatment to a tissue site includes a manifold delivery tube and a balloon having an inner space. The balloon is capable of assuming collapsed and expanded positions. The system further includes a manifold having a plurality of flow channels. The manifold is disposed within the inner space of the balloon. A sharp tip is configured to be delivered within the manifold delivery tube to puncture the balloon.

In another embodiment, a reduced pressure delivery system for applying reduced pressure tissue treatment to a tissue site includes a reduced pressure delivery tube for delivering reduced pressure to the tissue site. A manifold having a plurality of flow channels surrounds the reduced pressure delivery tube. The manifold is fluidly connected to the reduced pressure delivery tube. An impermeable membrane surrounds the manifold, and the impermeable membrane is capable of assuming compressed, relaxed, and expanded positions. The system further includes a manifold delivery tube configured to deliver the reduced pressure delivery tube, the manifold, and the impermeable membrane to the tissue site.

In yet another embodiment, a reduced pressure delivery system for applying reduced pressure tissue treatment to a tissue site includes a manifold delivery tube having a distal end. The distal end is configured to be positioned at the tissue site. A balloon having an inner space is provided and is capable of assuming collapsed and expanded positions. The system further includes a manifold having a plurality of flow channels, the manifold being disposed within the inner space of the balloon. The balloon and the manifold are configured to be delivered to the tissue site through the manifold delivery tube.

In still another embodiment, a reduced pressure delivery system for applying reduced pressure tissue treatment to a tissue site includes a manifold delivery tube having at least two lumens. A manifold having a plurality of flow channels is provided, the manifold being disposed within a first of the lumens of the manifold delivery tube. A balloon having an inner space is provided and is capable of assuming collapsed and expanded positions. The inner space of the balloon is fluidly connected to a second of the lumens of the manifold delivery tube. The manifold further includes (1) a flexible wall surrounding a primary flow passage and adapted to be placed in proximity to the tissue site, the flexible wall including a plurality of apertures through the flexible wall and communicating with the primary flow passage; (2) a blockage prevention member positioned within the primary flow passage; (3) a first conduit having at least one outlet fluidly connected to the primary flow passage to deliver reduced pressure to the primary flow passage; and (4) a second conduit having at least one outlet proximate the primary flow passage or the at least one outlet of the first conduit to purge at least one of the primary flow passage and the outlet of the first conduit with a gaseous fluid during the application of reduced pressure.

Other objects, features, and advantages of the present invention will become apparent with reference to the drawings and detailed description that follow.

BRIEF DESCRIPTION OF THE DRAWINGS

FIG. 8A illustrates a cross-sectional front view of a reduced pressure delivery apparatus according to an embodiment of the present invention;

FIG. 8B depicts a side view of the reduced pressure delivery apparatus of FIG. 8A;

FIG. 9 illustrates a front view of a reduced pressure delivery apparatus according to an embodiment of the present invention being used to apply a reduced pressure tissue treatment to a bone of a patient;

FIG. 32 depicts a cross-sectional front view of a reduced pressure delivery apparatus according to an embodiment of the present invention, the reduced pressure delivery apparatus including a hip prosthesis having a plurality of flow channels for applying a reduced pressure to an area of bone surrounding the hip prosthesis;

FIG. 33 illustrates a cross-sectional front view of the hip prosthesis of FIG. 32 having a second plurality of flow channels for delivering a fluid to the area of bone surrounding the hip prosthesis;

FIGS. 40-48 depict various views of a reduced pressure delivery system according to an embodiment of the present invention, the reduced pressure delivery system having a primary manifold that includes a flexible wall surrounding a primary flow passage and a plurality of apertures in the flexible wall;

FIGS. 49 and 50 illustrate perspective and top cross-sectional views of a reduced pressure delivery system according to an embodiment of the present invention, the reduced pressure delivery system having a primary manifold that is integrally connected to a reduced pressure delivery tube;

FIG. 51 depicts a perspective view of the primary manifolds of FIGS. 40-50 being applied with a secondary manifold to a bone tissue site; and FIG. 52 illustrates a schematic view of a reduced pressure delivery system having a valve fluidly connected to a second conduit according to an embodiment of the present invention.

DETAILED DESCRIPTION OF THE ILLUSTRATIVE EMBODIMENTS

Figure 1:
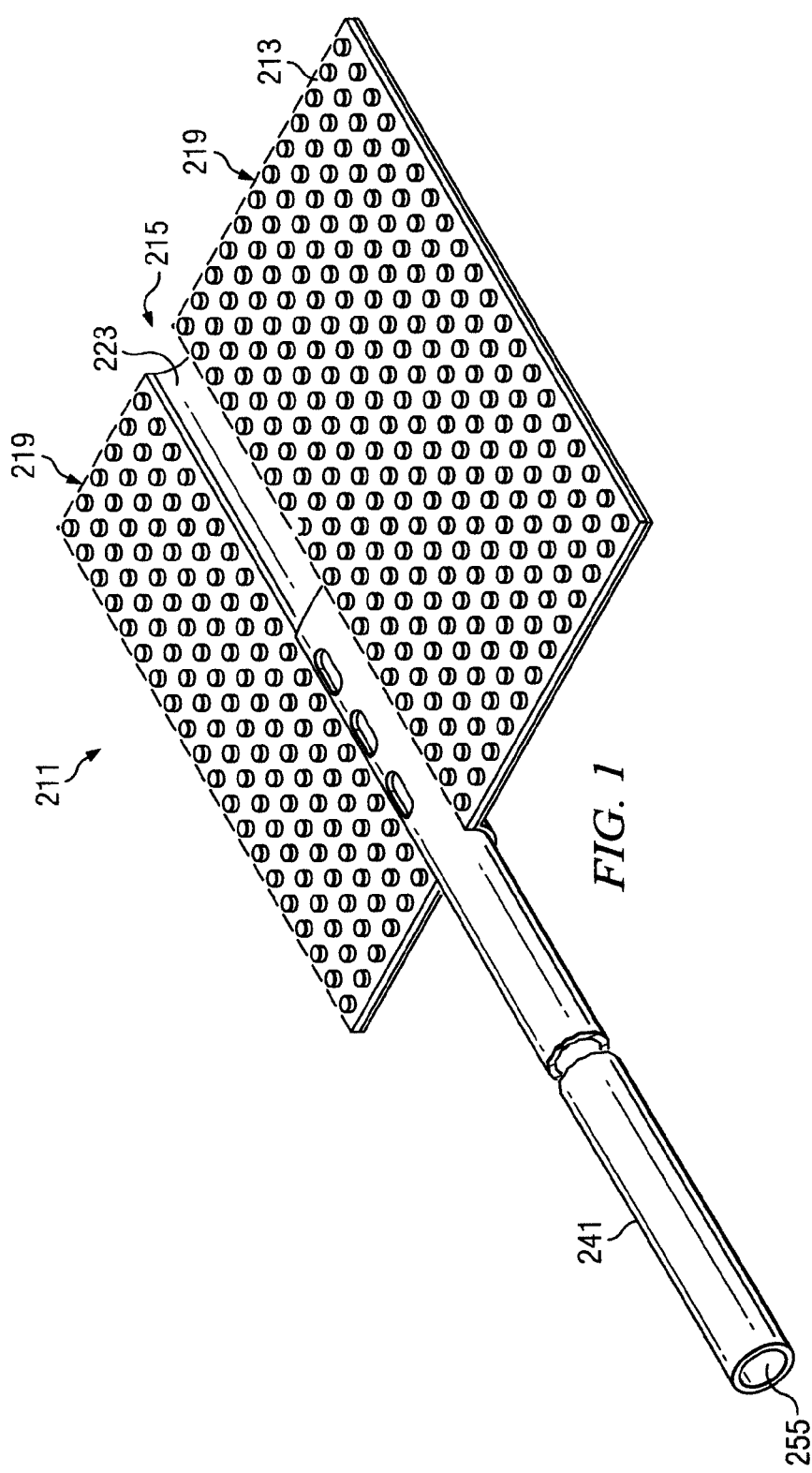
FIG. 1 depicts a perspective view of a reduced pressure delivery apparatus according to an embodiment of the present invention, the reduced pressure delivery apparatus having a plurality of projections extending from a flexible barrier to create a plurality of flow channels.
Figure 2:
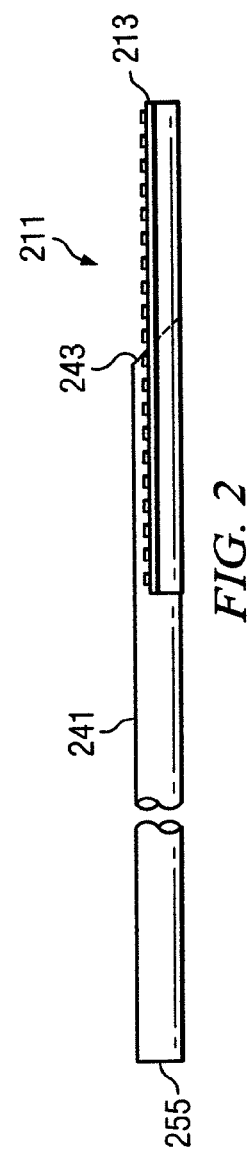
FIG. 2 illustrates a front view of the reduced pressure delivery apparatus of FIG. 1.
Figure 3:
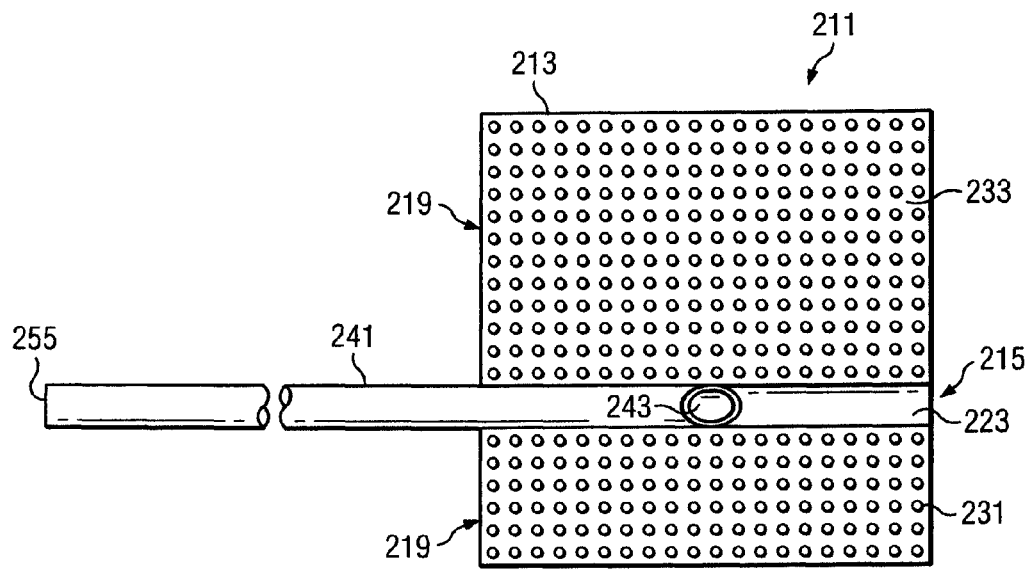
FIG. 3 depicts a top view of the reduced pressure delivery apparatus of FIG. 1.

In the following detailed description of the illustrative embodiments, reference is made to the accompanying drawings that form a part hereof, and in which is shown by way of illustration several embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the illustrative embodiments is defined only by the appended claims.

As used herein, the term "elastomeric" means having the properties of an elastomer. The term "elastomer" refers generally to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, and silicones.

As used herein, the term "flexible" refers to an object or material that is able to be bent or flexed. Elastomeric materials are typically flexible, but reference to flexible materials herein does not necessarily limit material selection to only elastomers. The use of the term "flexible" in connection with a material or reduced pressure delivery apparatus of the present invention generally refers to the material's ability to conform to or closely match the shape of a tissue site. For example, the flexible nature of a reduced pressure delivery apparatus used to treat a bone defect may allow the apparatus to be wrapped or folded around the portion of the bone having the defect.

The term "fluid" as used herein generally refers to a gas or liquid, but may also include any other flowable material, including but not limited to gels, colloids, and foams.

The term "impermeable" as used herein generally refers to the ability of a membrane, cover, sheet, or other substance to block or slow the transmission of either liquids or gas. Impermeability may be used to refer to covers, sheets, or other membranes that are resistant to the transmission of liquids, while allowing gases to transmit through the membrane. While an impermeable membrane may be liquid tight, the membrane may simply reduce the transmission rate of all or only certain liquids. The use of the term "impermeable" is not meant to imply that an impermeable membrane is above or below any particular industry standard measurement for impermeability, such as a particular value of water vapor transfer rate (WVTR).

The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam such as open-cell foam, porous tissue collections, and liquids, gels and foams that include or cure to include flow channels.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube and the area of the tissue site. As the hydrostatic pressure around the tissue site approaches the desired reduced pressure, the flow may subside, and the reduced pressure is then maintained. Unless otherwise indicated, values of pressure stated herein are gage pressures.

The term "scaffold" as used herein refers to a substance or structure used to enhance or promote the growth of cells and/or the formation of tissue. A scaffold is typically a three dimensional porous structure that provides a template for cell growth. The scaffold may be infused with, coated with, or comprised of cells, growth factors, or other nutrients to promote cell growth. A scaffold may be used as a manifold in accordance with the embodiments described herein to administer reduced pressure tissue treatment to a tissue site.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIGS. 1-5, a reduced pressure delivery apparatus, or wing manifold 211 according to the principles of the present invention includes a flexible barrier 213 having a spine portion 215 and a pair of wing portions 219. Each wing portion 219 is positioned along opposite sides of the spine portion 215. The spine portion 215 forms an arcuate channel 223 that may or may not extend the entire length of the wing manifold 211. Although the spine portion 215 may be centrally located on the wing manifold 211 such that the width of the wing portions 219 is equal, the spine portion 215 may also be offset as illustrated in FIGS. 1-5, resulting in one of the wing portions 219 being wider than the other wing portion 219. The extra width of one of the wing portions 219 may be particularly useful if the wing manifold 211 is being used in connection with bone regeneration or healing and the wider wing manifold 211 is to be wrapped around fixation hardware attached to the bone.

The flexible barrier 213 is preferably formed by an elastomeric material such as a silicone polymer. An example of a suitable silicone polymer includes MED-6015 manufactured by Nusil Technologies of Carpinteria, Calif. It should be noted, however, that the flexible barrier 213 could be made from any other biocompatible, flexible material. The flexible barrier 213 encases a flexible backing 227 that adds strength and durability to the flexible barrier 213. The thickness of the flexible barrier 213 encasing the flexible backing 227 may be less in the arcuate channel 223 than that in the wing portions 219. If a silicone polymer is used to form the flexible barrier 213, a silicone adhesive may also be used to aid bonding with the flexible backing 227. An example of a silicone adhesive could include MED-1011, also sold by Nusil Technologies. The flexible backing 227 is preferably made from a polyester knit fabric such as Bard 6013 manufactured by C.R. Bard of Tempe, Ariz. However, the flexible backing 227 could be made from any biocompatible, flexible material that is capable of adding strength and durability to the flexible barrier 213. Under certain circumstances, if the flexible barrier 213 is made from a suitably strong material, the flexible backing 227 could be omitted.

It is preferred that either the flexible barrier 213 or the flexible backing 227 be impermeable to liquids, air, and other gases, or alternatively, both the flexible backing 227 and the flexible barrier 213 may be impermeable to liquids, air, and other gases.

The flexible barrier 213 and flexible backing 227 may also be constructed from bioresorbable materials that do not have to be removed from a patient's body following use of the reduced pressure delivery apparatus 211. Suitable bioresorbable materials may include, without limitation, a polymeric blend of polylactic acid (PLA) and polyglycolic acid (PGA). The polymeric blend may also include without limitation polycarbonates, polyfumarates, and capralactones. The flexible barrier 213 and the flexible backing 227 may further serve as a scaffold for new cell-growth, or a scaffold material may be used in conjunction with the flexible barrier 213 and flexible backing 227 to promote cell-growth. Suitable scaffold material may include, without limitation, calcium phosphate, collagen, PLA/PGA, coral hydroxy apatites, carbonates, or processed allograft materials. Preferably, the scaffold material will have a high void-fraction (i.e. a high content of air).

In one embodiment the flexible backing 227 may be adhesively attached to a surface of the flexible barrier 213. If a silicone polymer is used to form the flexible barrier 213, a silicone adhesive may also be used to attach the flexible backing 227 to the flexible barrier 213. While an adhesive is the preferred method of attachment when the flexible backing 227 is surface bonded to the flexible barrier 213, any suitable attachment may be used.

The flexible barrier 213 includes a plurality of projections 231 extending from the wing portions 219 on a surface of the flexible barrier 213. The projections 231 may be cylindrical, spherical, hemispherical, cubed, or any other shape, as long as at least some portion of each projection 231 is in a plane different than the plane associated with the side of the flexible backing 213 to which the projections 231 are attached. In this regard, a particular projection 231 is not even required to have the same shape or size as other projections 231; in, fact, the projections 231 may include a random mix of different shapes and sizes. Consequently, the distance by which each projection 231 extends from the flexible barrier 213 could vary, but may also be uniform among the plurality of projections 231.

The placement of projections 231 on the flexible barrier 213 creates a plurality of flow channels 233 between the projections. When the projections 231 are of uniform shape and size and are spaced uniformly on the flexible barrier 213, the flow channels 233 created between the projections 231 are similarly uniform. Variations in the size, shape, and spacing of the projections 231 may be used to alter the size and flow characteristics of the flow channels 233.

Figure 5:
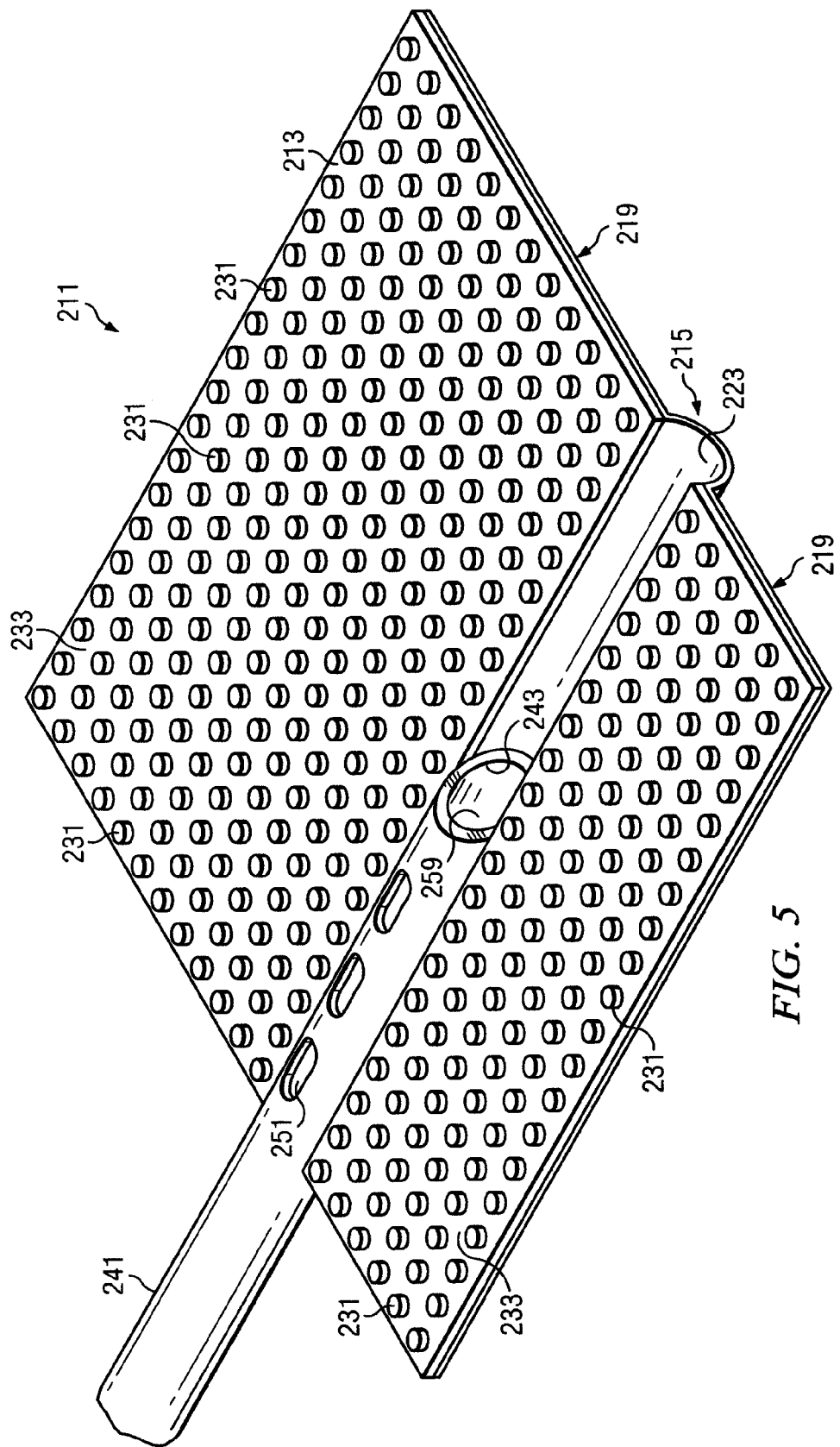
FIG. 5 illustrates an enlarged perspective view of the reduced pressure delivery apparatus of FIG. 1.

A reduced-pressure delivery tube 241 is positioned within the arcuate channel 223 and is attached to the flexible barrier 213 as illustrated in FIG. 5. The reduced-pressure delivery tube 241 may be attached solely to the flexible barrier 213 or the flexible backing 227, or the tube 241 could be attached to both the flexible barrier 213 and the flexible backing 227. The reduced-pressure delivery tube 241 includes a distal orifice 243 at a distal end of the tube 241. The tube 241 may be positioned such that the distal orifice 243 is located at any point along the arcuate channel 223, but the tube 241 is preferably positioned such that the distal orifice 243 is located approximately midway along the longitudinal length of the arcuate channel 223. The distal orifice 243 is preferably made elliptical or oval in shape by cutting the tube 241 along a plane that is oriented less than ninety (90) degrees to the longitudinal axis of the tube 241. While the orifice 243 may also be round, the elliptical shape of the orifice 243 increases fluid communication with the flow channels 233 formed between the projections 231.

The reduced-pressure delivery tube 241 is preferably made from paralyne-coated silicone or urethane. However, any medical-grade tubing material may be used to construct the reduced-pressure delivery tube 241. Other coatings that may coat the tube include heparin, anti-coagulants, anti-fibrinogens, anti-adherents, anti-thrombinogens, and hydrophilic coatings.

In one embodiment, the reduced-pressure delivery tube 241 may also include vent openings, or vent orifices 251 positioned along the reduced-pressure delivery tube 241 as either an alternative to the distal orifice 243 or in addition to the distal orifice 243 to further increase fluid communication between the reduced-pressure delivery tube 241 and the flow channels 233. The reduced-pressure delivery tube 241 may be positioned along only a portion of the longitudinal length of the arcuate channel 223 as shown in FIGS. 1-5, or alternatively may be positioned along the entire longitudinal length of the arcuate channel 223. If positioned such that the reduced-pressure delivery tube 241 occupies the entire length of the arcuate channel 223, the distal orifice 243 may be capped such that all fluid communication between the tube 241 and the flow channels 233 occurs through the vent openings 251.

The reduced-pressure delivery tube 241 further includes a proximal orifice 255 at a proximal end of the tube 241. The proximal orifice 255 is configured to mate with a reduced-pressure source, which is described in more detail below with reference to FIG. 9. The reduced-pressure delivery tube 241 illustrated in FIGS. 1-3, 4A, and 5 includes only a single lumen, or passageway 259. It is possible, however, for the reduced-pressure delivery tube 241 to include multiple lumens such as a dual lumen tube 261 illustrated in FIG. 4B. The dual lumen tube 261 includes a first lumen 263 and a second lumen 265. The use of a dual lumen tube provides separate paths of fluid communication between the proximal end of the reduced-pressure delivery tube 241 and the flow channels 233. For example, the use of the dual lumen tube 261 may be used to allow communication between the reduced pressure source and the flow channels 233 along the first lumen 263. The second lumen 265 may be used to introduce a fluid to the flow channels 233. The fluid may be filtered air or other gases, antibacterial agents, antiviral agents, cell-growth promotion agents, irrigation fluids, chemically active fluids, or any other fluid. If it is desired to introduce multiple fluids to the flow channels 233 through separate fluid communication paths, a reduced-pressure delivery tube may be provided with more than two lumens.

Figure 4A:
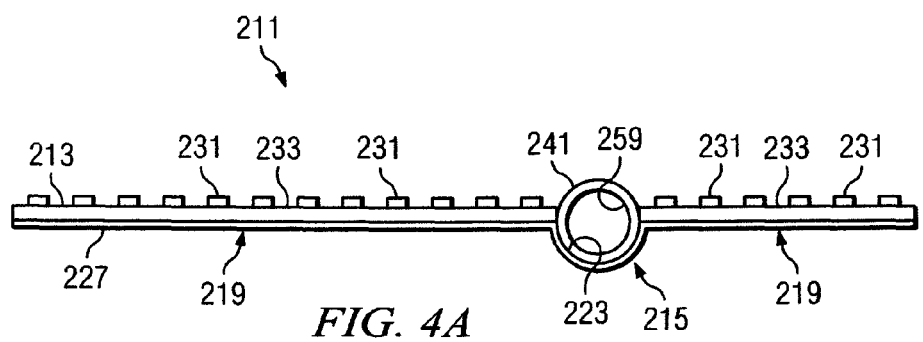
FIG. 4A illustrates a side view of the reduced pressure delivery apparatus of FIG. 1, the reduced pressure delivery apparatus having a single lumen, reduced-pressure delivery tube.
Figure 4B:
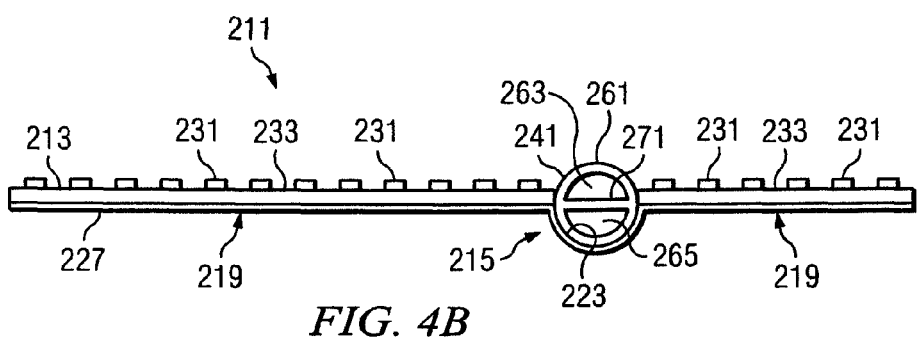
FIG. 4B depicts a side view of an alternative embodiment of the reduced pressure delivery apparatus of FIG. 1, the reduced pressure delivery apparatus having a dual lumen, reduced-pressure delivery tube.

Referring still to FIG. 4B, a horizontal divider 271 separates the first and second lumens 263, 265 of the reduced-pressure delivery tube 261, resulting in the first lumen 263 being positioned above the second lumen 265. The relative position of the first and second lumens 263, 265 may vary, depending on how fluid communication is provided between the lumens 263, 265 and the flow channels 233. For example, when the first lumen 263 is positioned as illustrated in FIG. 4B, vent openings similar to vent openings 251 may be provided to allow communication with the flow channels 233. When the second lumen 263 is positioned as illustrated in FIG. 4B, the second lumen 263 may communicate with the flow channels 233 through a distal orifice similar to distal orifice 243. Alternatively, the multiple lumens of a reduced-pressure delivery tube could be positioned side by side with a vertical divider separating the lumens, or the lumens could be arranged concentrically or coaxially.

It should be apparent to a person having ordinary skill in the art that the provision of independent paths of fluid communication could be accomplished in a number of different ways, including that of providing a multi-lumen tube as described above. Alternatively, independent paths of fluid communication may be provided by attaching a single lumen tube to another single lumen tube, or by using separate, unattached tubes with single or multiple lumens.

If separate tubes are used to provide separate paths of fluid communication to the flow channels 233, the spine portion 215 may include multiple arcuate channels 223, one for each tube. Alternatively the arcuate channel 223 may be enlarged to accommodate multiple tubes. An example of a reduced-pressure delivery apparatus having a reduced-pressure delivery tube separate from a fluid delivery tube is discussed in more detail below with reference to FIG. 9.

Figure 6:
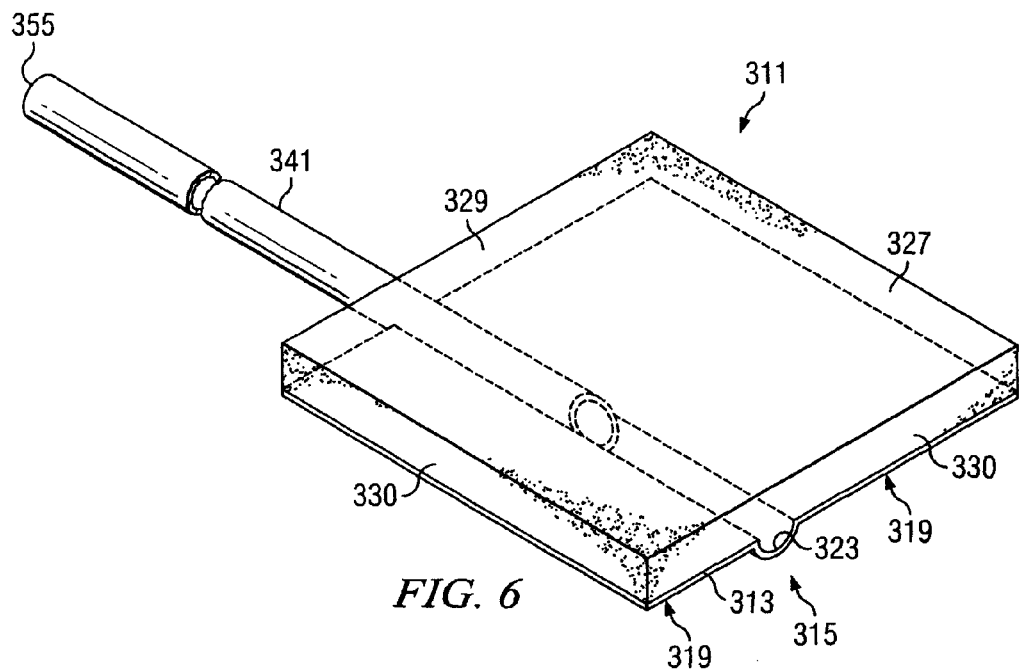
FIG. 6 depicts a perspective view of a reduced pressure delivery apparatus according to an embodiment of the present invention, the reduced pressure delivery apparatus having a cellular material attached to a flexible barrier having a spine portion and a pair of wing portions, the cellular material having a plurality of flow channels.
Figure 7:
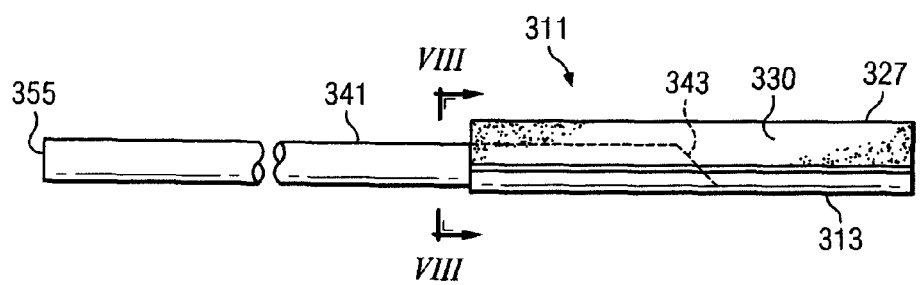
FIG. 7 illustrates a front view of the reduced pressure delivery apparatus of FIG. 6.
Figure 8:
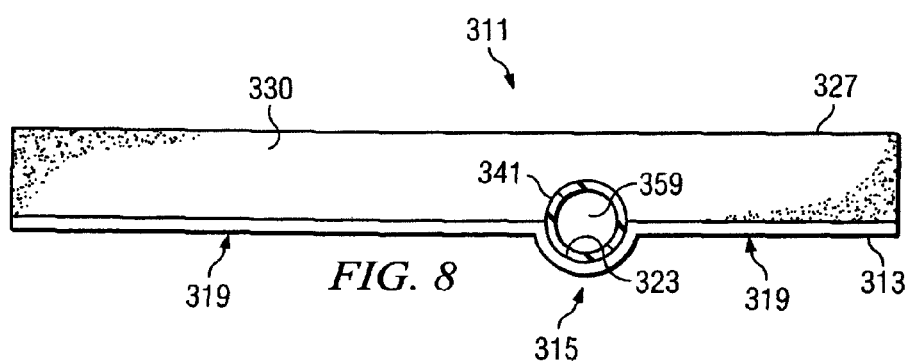
FIG. 8 depicts a cross-sectional side view of the reduced pressure delivery apparatus of FIG. 7 taken at XVII-XVII.

Referring to FIGS. 6-8, a reduced pressure delivery apparatus, or wing manifold 311 according to the principles of the present invention includes a flexible barrier 313 having a spine portion 315 and a pair of wing portions 319. Each wing portion 319 is positioned along opposite sides of the spine portion 315. The spine portion 315 forms an arcuate channel 323 that may or may not extend the entire length of the wing manifold 311. Although the spine portion 315 may be centrally located on the wing manifold 311 such that the size of the wing portions 319 is equal, the spine portion 315 may also be offset as illustrated in FIGS. 6-8, resulting in one of the wing portions 319 being wider than the other wing portion 319. The extra width of one of the wing portions 319 may be particularly useful if the wing manifold 311 is being used in connection with bone regeneration or healing and the wider wing manifold 311 is to be wrapped around fixation hardware attached to the bone.

A cellular material 327 is attached to the flexible barrier 313 and may be provided as a single piece of material that covers the entire surface of the flexible barrier 313, extending across the spine portion 315 and both wing portions 319. The cellular material 327 includes an attachment surface (not visible in FIG. 6) that is disposed adjacent to the flexible barrier 313, a main distribution surface 329 opposite the attachment surface, and a plurality of perimeter surfaces 330.

In one embodiment the flexible barrier 313 may be similar to flexible barrier 213 and include a flexible backing. While an adhesive is a preferred method of attaching the cellular material 327 to the flexible barrier 313, the flexible barrier 313 and cellular material 327 could be attached by any other suitable attachment method or left for the user to assemble at the site of treatment. The flexible barrier 313 and/or flexible backing serve as an impermeable barrier to transmission of fluids such as liquids, air, and other gases.

In one embodiment, a flexible barrier and flexible backing may not be separately provided to back the cellular material 327. Rather, the cellular material 327 may have an integral barrier layer that is an impermeable portion of the cellular material 327. The barrier layer could be formed from closed-cell material to prevent transmission of fluids, thereby substituting for the flexible barrier 313. If an integral barrier layer is used with the cellular material 327, the barrier layer may include a spine portion and wing portions as described previously with reference to the flexible barrier 313.

The flexible barrier 313 is preferably made from an elastomeric material such as a silicone polymer. An example of a suitable silicone polymer includes MED-6015 manufactured by Nusil Technologies of Carpinteria, Calif. It should be noted, however, that the flexible barrier 313 could be made from any other biocompatible, flexible material. If the flexible barrier encases or otherwise incorporates a flexible backing, the flexible backing is preferably made from a polyester knit fabric such as Bard 6013 manufactured by C.R. Bard of Tempe, Ariz. However, the flexible backing 227 could be made from any biocompatible, flexible material that is capable of adding strength and durability to the flexible barrier 313.

In one embodiment, the cellular material 327 is an open-cell, reticulated polyetherurethane foam with pore sizes ranging from about 400-600 microns. An example of this foam may include GranuFoam manufactured by Kinetic Concepts, Inc. of San Antonio, Tex. The cellular material 327 may also be gauze, felted mats, or any other biocompatible material that provides fluid communication through a plurality of channels in three dimensions.

The cellular material 327 is primarily an "open cell" material that includes a plurality of cells fluidly connected to adjacent cells. A plurality of flow channels is formed by and between the "open cells" of the cellular material 327. The flow channels allow fluid communication throughout that portion of the cellular material 327 having open cells. The cells and flow channels may be uniform in shape and size, or may include patterned or random variations in shape and size. Variations in shape and size of the cells of the cellular material 327 result in variations in the flow channels, and such characteristics can be used to alter the flow characteristics of fluid through the cellular material 327. The cellular material 327 may further include portions that include "closed cells." These closed-cell portions of the cellular material 327 contain a plurality of cells, the majority of which are not fluidly connected to adjacent cells. An example of a closed-cell portion is described above as a barrier layer that may be substituted for the flexible barrier 313. Similarly, closed-cell portions could be selectively disposed in the cellular material 327 to prevent transmission of fluids through the perimeter surfaces 330 of the cellular material 327.

The flexible barrier 313 and cellular material 327 may also be constructed from bioresorbable materials that do not have to be removed from a patient's body following use of the reduced pressure delivery apparatus 311. Suitable bioresorbable materials may include, without limitation, a polymeric blend of polylactic acid (PLA) and polyglycolic acid (PGA). The polymeric blend may also include without limitation polycarbonates, polyfumarates, and capralactones. The flexible barrier 313 and the cellular material 327 may further serve as a scaffold for new cell-growth, or a scaffold material may be used in conjunction with the flexible barrier 313, flexible backing 327, and/or cellular material 327 to promote cell-growth. Suitable scaffold materials may include, without limitation, calcium phosphate, collagen, PLA/PGA, coral hydroxy apatites, carbonates, or processed allograft materials. Preferably, the scaffold material will have a high void-fraction (i.e. a high content of air).

A reduced-pressure delivery tube 341 is positioned within the arcuate channel 323 and is attached to the flexible barrier 313. The reduced-pressure delivery tube 341 may also be attached to the cellular material 327, or in the case of only a cellular material 327 being present, the reduced-pressure delivery tube 341 may be attached to only the cellular material 327. The reduced-pressure delivery tube 341 includes a distal orifice 343 at a distal end of the tube 341 similar to the distal orifice 243 of FIG. 5. The reduced-pressure delivery tube 341 may be positioned such that the distal orifice 343 is located at any point along the arcuate channel 323, but is preferably located approximately midway along the longitudinal length of the arcuate channel 323. The distal orifice 343 is preferably made elliptical or oval in shape by cutting the tube 341 along a plane that is oriented less than ninety (90) degrees to the longitudinal axis of the tube 341. While the orifice may also be round, the elliptical shape of the orifice increases fluid communication with the flow channels in the cellular material 327.

In one embodiment, the reduced-pressure delivery tube 341 may also include vent openings, or vent orifices (not shown) similar to vent openings 251 of FIG. 5. The vent openings are positioned along the tube 341 as either an alternative to the distal orifice 343 or in addition to the distal orifice 343 to further increase fluid communication between the reduced-pressure delivery tube 341 and the flow channels. As previously described, the reduced-pressure delivery tube 341 may be positioned along only a portion of the longitudinal length of the arcuate channel 323, or alternatively may be positioned along the entire longitudinal length of the arcuate channel 323. If positioned such that the reduced-pressure delivery tube 341 occupies the entire arcuate channel 323, the distal orifice 343 may be capped such that all fluid communication between the tube 341 and the flow channels occurs through the vent openings.

Preferably, the cellular material 327 overlays and directly contacts the reduced-pressure delivery tube 341. The cellular material 327 may be connected to the reduced-pressure delivery tube 341, or the cellular material 327 may simply be attached to the flexible barrier 313. If the reduced-pressure delivery tube 341 is positioned such that it only extends to a midpoint of the arcuate channel 323, the cellular material 327 may also be connected to the spine portion 315 of the flexible barrier 313 in that area of the arcuate channel 323 that does not contain the reduced-pressure delivery tube 341.

The reduced-pressure delivery tube 341 further includes a proximal orifice 355 at a proximal end of the tube 341. The proximal orifice 355 is configured to mate with a reduced-pressure source, which is described in more detail below with reference to FIG. 9. The reduced-pressure delivery tube 341 illustrated in FIGS. 6-8 includes only a single lumen, or passageway 359. It is possible, however, for the reduced-pressure delivery tube 341 to include multiple lumens such as those described previously with reference to FIG. 4B. The use of a multiple lumen tube provides separate paths of fluid communication between the proximal end of the reduced-pressure delivery tube 341 and the flow channels as previously described. These separate paths of fluid communication may also be provided by separate tubes having single or multiple lumens that communicate with the flow channels.

Referring to FIGS. 8A and 8B, a reduced pressure delivery apparatus 371 according to the principles of the present invention includes a reduced pressure delivery tube 373 having an extension portion 375 at a distal end 377 of the reduced pressure delivery tube 373. The extension portion 375 is preferably arcuately shaped to match the curvature of the reduced pressure delivery tube 373. The extension portion 375 may be formed by removing a portion of the reduced pressure delivery tube 373 at the distal end 377, thereby forming a cut-out 381 having a shoulder 383. A plurality of projections 385 is disposed on an inner surface 387 of the reduced pressure delivery tube 373 to form a plurality of flow channels 391 between the projections 385. The projections 385 may be similar in size, shape, and spacing as the projections described with reference to FIGS. 1-5. The reduced pressure delivery apparatus 371 is particularly suited for applying reduced pressure to and regenerating tissue on connective tissues that are capable of being received within the cut-out 381. Ligaments, tendons, and cartilage are non-limiting examples of the tissues that may be treated by reduced pressure delivery apparatus 371.

Referring to FIG. 9, a reduced pressure delivery apparatus 411 similar to the other reduced pressure delivery apparatuses described herein is used to apply a reduced pressure tissue treatment to a tissue site 413, such as a human bone 415 of a patient. When used to promote bone tissue growth, reduced pressure tissue treatment can increase the rate of healing associated with a fracture, a non-union, a void, or other bone defects. It is further believed that reduced pressure tissue treatment may be used to improve recovery from osteomyelitis. The therapy may further be used to increase localized bone densities in patients suffering from osteoporosis. Finally, reduced pressure tissue treatment may be used to speed and improve oseointegration of orthopedic implants such as hip implants, knee implants, and fixation devices.

Referring still to FIG. 9, the reduced pressure delivery apparatus 411 includes a reduced-pressure delivery tube 419 having a proximal end 421 fluidly connected to a reduced pressure source 427. The reduced pressure source 427 is a pump or any other device that is capable of applying a reduced pressure to the tissue site 413 through the reduced pressure delivery tube 419 and a plurality of flow channels associated with the reduced pressure delivery apparatus 411. Applying reduced pressure to the tissue site 413 is accomplished by placing the wing portions of the reduced pressure delivery apparatus 411 adjacent the tissue site 413, which in this particular example involves wrapping the wing portions around a void defect 429 in the bone 415. The reduced pressure delivery apparatus 411 may be surgically or percutaneously inserted. When percutaneously inserted, the reduced-pressure delivery tube 419 is preferably inserted through a sterile insertion sheath that penetrates the skin tissue of the patient.

The application of reduced pressure tissue treatment typically generates granulation tissue in the area surrounding the tissue site 413. Granulation tissue is a common tissue that often forms prior to tissue repair in the body. Under normal circumstances, granulation tissue may form in response to a foreign body or during wound healing. Granulation tissue typically serves as a scaffold for healthy replacement tissue and further results in the development of some scar tissue. Granulation tissue is highly vascularized, and the increased growth and growth rate of the highly vascularized tissue in the presence of reduced pressure promotes new tissue growth at the tissue site 413.

Referring still to FIG. 9, a fluid delivery tube 431 may be fluidly connected at a distal end to the flow channels of the reduced pressure delivery apparatus 411. The fluid delivery tube 431 includes a proximal end 432 that is fluidly connected to a fluid delivery source 433. If the fluid being delivered to the tissue site is air, the air is preferably filtered by a filter 434 capable of filtering particles at least as small as 0.22 µm in order to clean and sterilize the air. The introduction of air to the tissue site 413, especially when the tissue site 413 is located beneath the surface of the skin, is important to facilitate good drainage of the tissue site 413, thereby reducing or preventing obstruction of the reduced pressure delivery tube 419. The fluid delivery tube 431 and fluid delivery source 433 could also be used to introduce other fluids to the tissue site 413, including without limitation an antibacterial agent, an antiviral agent, a cell-growth promotion agent, an irrigation fluid, or other chemically active agents. When percutaneously inserted, the fluid delivery tube 431 is preferably inserted through a sterile insertion sheath that penetrates the skin tissue of the patient.

A pressure sensor 435 may be operably connected to the fluid delivery tube 431 to indicate whether the fluid delivery tube 431 is occluded with blood or other bodily fluids. The pressure sensor 435 may be operably connected to the fluid delivery source 433 to provide feedback so that the amount of fluid introduced to the tissue site 413 is controlled. A check valve (not shown) may also be operably connected near the distal end of the fluid delivery tube 431 to prevent blood or other bodily fluids from entering the fluid delivery tube 431.

The independent paths of fluid communication provided by reduced pressure delivery tube 419 and fluid delivery tube 431 may be accomplished in a number of different ways, including that of providing a single, multi-lumen tube as described previously with reference to FIG. 4B. A person of ordinary skill in the art will recognize that the sensors, valves, and other components associated with the fluid delivery tube 431 could also be similarly associated with a particular lumen in the reduced pressure delivery tube 419 if a multi-lumen tube is used. It is preferred that any lumen or tube that fluidly communicates with the tissue site be coated with an anticoagulent to prevent a build-up of bodily fluids or blood within the lumen or tube. Other coatings that may coat the lumens or tubes include without limitation heparin, anti-coagulants, anti-fibrinogens, anti-adherents, anti-thrombinogens, and hydrophilic coatings.

Referring to FIGS. 10-19, testing has shown the positive effects of reduced pressure tissue treatment when applied to bone tissue. In one particular test, reduced pressure tissue treatment was applied to the cranium of several rabbits to determine its effect on bone growth and regeneration. The specific goals of the test were to discover the effect of reduced pressure tissue treatment on rabbits having no defect on or injury to the cranium, the effect of reduced pressure tissue treatment on rabbits having critical-size defects on the cranium, and the effect of using a scaffold material with reduced pressure tissue treatment to treat critical-size defects on the cranium. The specific testing protocol and number of rabbits are listed below in Table 1.

TABLE 1

| | Testing Protocol |
|---|---|
| No. of Rabbits | Protocol |
| 4 | No defect on cranium; reduced pressure tissue treatment (RPTT) applied through cellular foam (GranuFoam) on top of intact periosteum for 6 days followed by immediate tissue harvest |
| 4 | No defect on cranium; cellular foam (GranuFoam) placed on top of intact periosteum without RPTT (control) for 6 days followed by immediate tissue harvest |
| 4 | One critical-size defect with stainless-steel screen placed on defect; one critical-size defect with calcium phosphate scaffold placed in defect; 24 hours RPTT applied to both defects; tissue harvest 2 weeks post-surgery |
| 4 | One critical-size defect with stainless-steel screen placed on defect; one critical-size defect with calcium phosphate scaffold placed in defect; 24 hours RPTT applied to both defects; tissue harvest 12 weeks post-surgery |
| 4 | One critical-size defect with stainless-steel screen placed on defect; one critical-size defect with calcium phosphate scaffold placed in defect; 6 days RPTT applied to both defects; tissue harvest 2 weeks post-surgery |
| 4 | One critical-size defect with stainless-steel screen placed on defect; one critical-size defect with calcium phosphate scaffold placed in defect; 6 days RPTT applied to both defects; tissue harvest 12 weeks post-surgery |

TABLE 1-continued

Testing Protocol

| No. of Rabbits | Protocol |
|---|---|
| 4 | One critical-size defect with stainless-steel screen placed on defect; one critical-size defect with calcium phosphate scaffold placed in defect; no RPTT applied (control); tissue harvest 2 weeks post-surgery |
| 4 | One critical-size defect with stainless-steel screen placed on defect; one critical-size defect with calcium phosphate scaffold placed in defect; no RPTT applied (control); tissue harvest 12 weeks post-surgery |
| 4 | Native control (no surgery; no RPTT) |
| 4 | Sham surgery (no defects, no RPTT); tissue harvest 6 days post-surgery |

Critical-size defects are defects in a tissue (e.g. the cranium), the size of which is large enough that the defect will not heal solely by in-life recovery. For rabbits, boring a full-thickness hole through the cranium that is approximately 15 mm in diameter creates a critical-size defect of the cranium.

Figure 10:
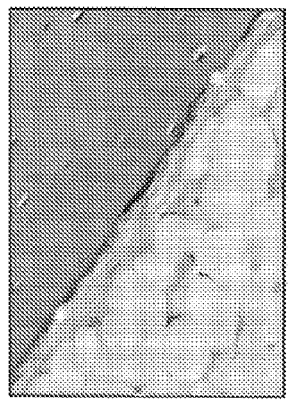
FIG. 10 depicts a histological section of a rabbit cranium showing naive, undamaged bone.
Figure 11:
FIG. 11 illustrates a histological section of a rabbit cranium showing induction of granulation tissue after application of reduced pressure tissue treatment.
Figure 12:
FIG. 12 depicts a histological section of a rabbit cranium showing deposition of new bone following application of reduced pressure tissue treatment.
Figure 13:
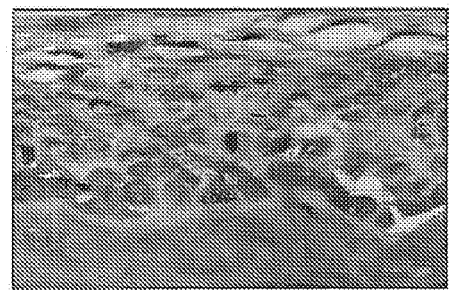
FIG. 13 illustrates a histological section of a rabbit cranium showing deposition of new bone following application of reduced pressure tissue treatment.

Referring more specifically to FIG. 10, a histological section of a rabbit cranium having naïve, undamaged bone is illustrated. The bone tissue of the cranium is colored magenta, the surrounding soft tissue white, and the layer of periosteum is highlighted by yellow asterisks. In FIG. 11, the rabbit cranium is illustrated following the application of reduced pressure tissue treatment for 6 days followed by immediate tissue harvest. The bone and periosteum are visible, and a layer of granulation tissue has developed. In FIG. 12, the rabbit cranium is illustrated following the application of reduced pressure tissue treatment for 6 days and followed by immediate tissue harvest. The histological section of FIG. 12 is characterized by the development of new bone tissue underlying the granulation tissue. The bone tissue is highlighted by yellow asterisks. In FIG. 13, the rabbit cranium is illustrated following the application of reduced pressure tissue treatment for 6 days followed by immediate tissue harvest. The new bone and periosteum are visible. This histological appearance of bone tissue development in response to reduced pressure tissue treatment is very similar to the histological appearance of bone development in a very young animal that is undergoing very rapid growth and deposition of new bone.

Figure 14:
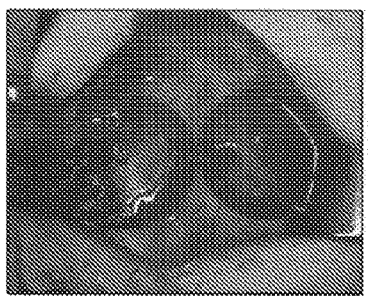
FIG. 14 depicts a photograph of a rabbit cranium having two critical size defects formed in the cranium.
Figure 15:
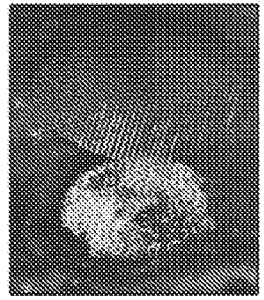
FIG. 15 illustrates a photograph of the rabbit cranium of FIG. 14 showing a calcium phosphate scaffold inserted within one of the critical size defects and a stainless steel screen overlaying the second of the critical size defects.
Figure 16:
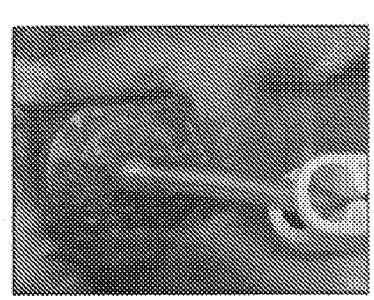
FIG. 16 depicts a photograph of the rabbit cranium of FIG. 14 showing the application of reduced pressure tissue treatment to the critical size defects.
Figure 17:
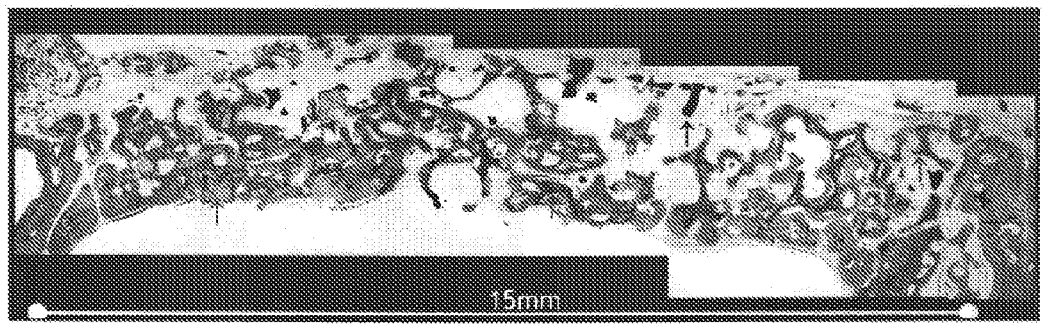
FIG. 17 illustrates a histological section of a rabbit cranium following reduced pressure tissue treatment, the histological section showing deposition of new bone within the calcium phosphate scaffold.

Referring more specifically to FIGS. 14-19, several photographs and histological sections are illustrated showing the procedures and results of reduced pressure tissue treatment on a rabbit cranium having critical-size defects. In FIG. 14, a rabbit cranium is illustrated on which two critical-size defects have been created. The full-thickness critical-size defects are approximately 15 mm in diameter. In FIG. 15, a stainless-steel screen has been placed over one of the critical-size defects, and a calcium phosphate scaffold has been placed within the second critical-size defect. In FIG. 16, a reduced pressure tissue treatment apparatus similar to those described herein is used to apply reduced pressure to the critical-size defects. The amount of pressure applied to each defect was −125 mm Hg gauge pressure. The reduced pressure was applied according to one of the protocols listed in Table 1. In FIG. 17, a histological section of cranium following six-day reduced pressure tissue treatment and twelve week post-surgery harvest is illustrated. The section illustrated includes calcium phosphate scaffold, which is indicated by red arrows. The application of reduced pressure tissue treatment resulted in the significant growth of new bone tissue, which is highlighted in FIG. 17 by yellow asterisks. The amount of bone growth is significantly greater than in critical-size defects containing identical calcium phosphate scaffolds but which were not treated with reduced pressure tissue treatment. This observation suggests there may be a threshold level or duration of therapy required to elicit a prolific new-bone response. Effects of reduced pressure tissue treatment are most pronounced in the specimens collected 12 weeks post-surgery, indicating the reduced pressure tissue treatment initiates a cascade of biological events leading to enhanced formation of new bone tissue.

Figure 18:
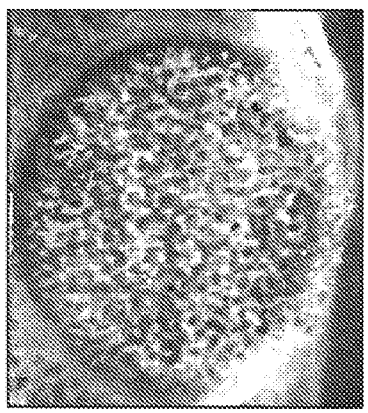
FIG. 18 depicts a radiograph of the scaffold-filled, critical size defect of FIG. 15 following six days of reduced pressure tissue treatment and two weeks post surgery.
Figure 19:
FIG. 19 illustrates a radiograph of the scaffold-filled, critical size defect of FIG. 15 following six days of reduced pressure tissue treatment and twelve weeks post surgery.

Critical-size defects covered with stainless steel screens (FIG. 15) but without scaffold material in the defect served as intra-animal controls with minimal new-bone growth. These data highlight the advantage of an appropriate scaffold material and the positive effect of reduced pressure tissue treatment on scaffold integration and biological performance. In FIGS. 18 and 19, radiographs of scaffold-filled, critical-size defects are illustrated following six days of reduced pressure tissue treatment. FIG. 18 illustrates the defect two weeks post-surgery and indicates some new bone deposition within the scaffold. The primary structure of the scaffold is still evident. FIG. 19 illustrates the defect twelve weeks post surgery and shows almost complete healing of the critical-size defect and a near complete loss of the primary scaffold architecture due to tissue integration, i.e. new bone formation within the scaffold matrix.

Figure 20:
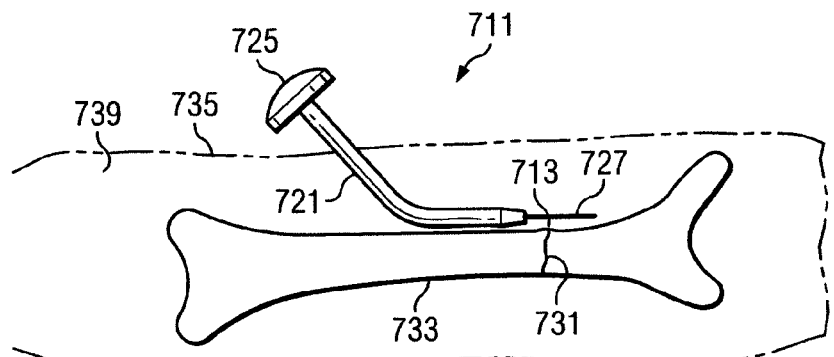
FIG. 20 depicts a front view of a reduced pressure delivery system according to an embodiment of the present invention, the reduced pressure delivery system having a manifold delivery tube that is used to percutaneously insert a reduced pressure delivery apparatus to a tissue site.

Referring to FIG. 20, a reduced pressure delivery system 711 according to an embodiment of the present invention delivers reduced pressure tissue treatment to a tissue site 713 of a patient. The reduced pressure delivery system 711 includes a manifold delivery tube 721. The manifold delivery tube 721 may be a catheter or cannula and may include features such as a steering unit 725 and a guide wire 727 that allow the manifold delivery tube 721 to be guided to the tissue site 713. Placement and direction of the guide wire 727 and the manifold delivery tube 721 may be accomplished by using endoscopy, ultrasound, fluoroscopy, auscultation, palpation, or any other suitable localization technique. The manifold delivery tube 721 is provided to percutaneously insert a reduced pressure delivery apparatus to the tissue site 713 of the patient. When percutaneously inserted, the manifold delivery tube 721 is preferably inserted through a sterile insertion sheath that penetrates the skin tissue of the patient.

In FIG. 20, the tissue site 713 includes bone tissue adjacent a fracture 731 on a bone 733 of the patient. The manifold delivery tube 721 is inserted through the patient's skin 735 and any soft tissue 739 surrounding the bone 733. As previously discussed, the tissue site 713 may also include any other type of tissue, including without limitation adipose tissue, muscle tissue, neural tissue, dermal tissue, vascular tissue, connective tissue, cartilage, tendons, or ligaments.

Figure 21:
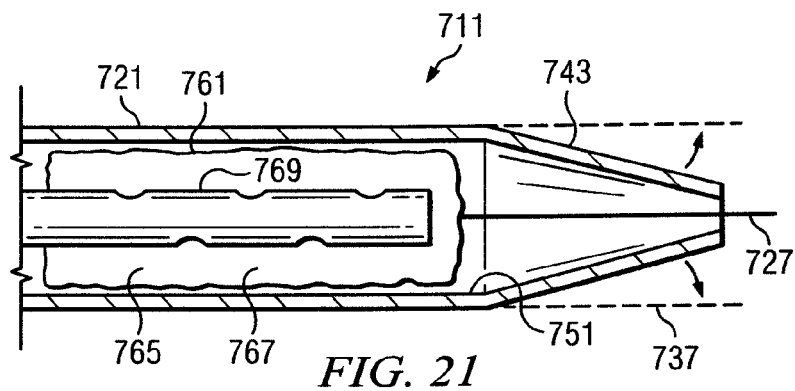
FIG. 21 illustrates an enlarged front view of the manifold delivery tube of FIG. 20, the manifold delivery tube containing a reduced pressure delivery apparatus having a flexible barrier and/or a cellular material in a compressed position.
Figure 22:
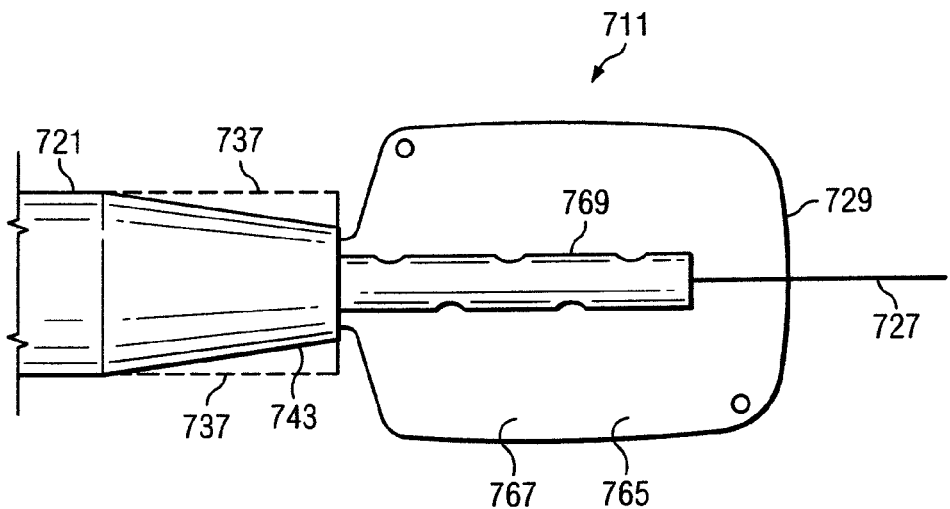
FIG. 22 depicts an enlarged front view of the manifold delivery tube of FIG. 21, the flexible barrier and/or cellular material of the reduced pressure delivery apparatus being shown in an expanded position after having been pushed from the manifold delivery tube.

Referring to FIGS. 21 and 22, the reduced pressure delivery system 711 is further illustrated. The manifold delivery tube 721 may include a tapered distal end 743 to ease insertion through the patient's skin 735 and soft tissue 739. The tapered distal end 743 may further be configured to flex radially outward to an open position such that the inner diameter of the distal end 743 would be substantially the same as or greater than the inner diameter at other portions of the tube 721. The open position of the distal end 743 is schematically illustrated in FIG. 21 by broken lines 737.

The manifold delivery tube 721 further includes a passageway 751 in which a reduced pressure delivery apparatus 761, or any other reduced pressure delivery apparatus, is contained. The reduced pressure delivery apparatus 761 includes a flexible barrier 765 and/or cellular material 767 similar to that described with reference to FIGS. 6-8. The flexible barrier 765 and/or cellular material 767 is preferably rolled, folded, or otherwise compressed around a reduced pressure delivery tube 769 to reduce the cross-sectional area of the reduced pressure delivery apparatus 761 within the passageway 751.

The reduced pressure delivery apparatus 761 may be placed within the passageway 751 and guided to the tissue site 713 following the placement of the distal end 743 manifold delivery tube 721 at the tissue site 713. Alternatively, the reduced pressure delivery apparatus 761 may be pre-positioned within the passageway 751 prior to the manifold delivery tube 721 being inserted into the patient. If the reduced pressure delivery apparatus 761 is to be pushed through the passageway 751, a biocompatible lubricant may be used to reduce friction between the reduced pressure delivery apparatus 761 and the manifold delivery tube 721. When the distal end 743 has been positioned at the tissue site 713 and the reduced pressure delivery apparatus 761 has been delivered to the distal end 743, the reduced pressure delivery apparatus 761 is then pushed toward the distal end 743, causing the distal end 743 to expand radially outward into the open position. The reduced pressure delivery apparatus 761 is pushed out of the manifold delivery tube 721, preferably into a void or space adjacent the tissue site 713. The void or space is typically formed by dissection of soft tissue, which may be accomplished by percutaneous means. In some cases, the tissue site 713 may be located at a wound site, and a void may be naturally present due to the anatomy of the wound. In other instances, the void may be created by balloon dissection, sharp dissection, blunt dissection, hydrodissection, pneumatic dissection, ultrasonic dissection, electrocautery dissection, laser dissection, or any other suitable dissection technique. When the reduced pressure delivery apparatus 761 enters the void adjacent the tissue site 713, the flexible barrier 765 and/or cellular material 767 of the reduced pressure delivery apparatus 761 either unrolls, unfolds, or decompresses (see FIG. 22) such that the reduced pressure delivery apparatus 761 can be placed in contact with the tissue site 713. Although not required, the flexible barrier 765 and/or cellular material 767 may be subjected to a vacuum or reduced pressure supplied through the reduced pressure delivery tube 769 to compress the flexible barrier 765 and/or cellular material 767. The unfolding of the flexible barrier 765 and/or cellular material 767 may be accomplished by either relaxing the reduced pressure supplied through the reduced pressure delivery tube 769 or by supplying a positive pressure through the reduced pressure delivery tube 769 to assist the unrolling process. Final placement and manipulation of the reduced pressure delivery apparatus 761 may be accomplished by using endoscopy, ultrasound, fluoroscopy, auscultation, palpation, or any other suitable localization technique. Following placement of the reduced pressure delivery apparatus 761, the manifold delivery tube 721 is preferably removed from the patient, but the reduced pressure delivery tube associated with reduced pressure delivery apparatus 761 remains in situ to allow percutaneous application of reduced pressure to the tissue site 713.

Figure 23:
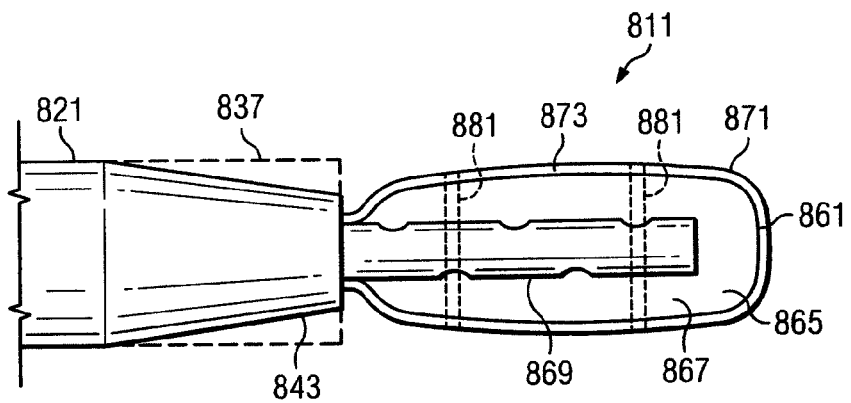
FIG. 23 illustrates a front view of a reduced pressure delivery system according to an embodiment of the present invention, the reduced pressure delivery system having a manifold delivery tube that is used to percutaneously insert a reduced pressure delivery apparatus to a tissue site, the reduced pressure delivery apparatus being shown outside of the manifold delivery tube but constrained by an impermeable membrane in a compressed position.
Figure 24:
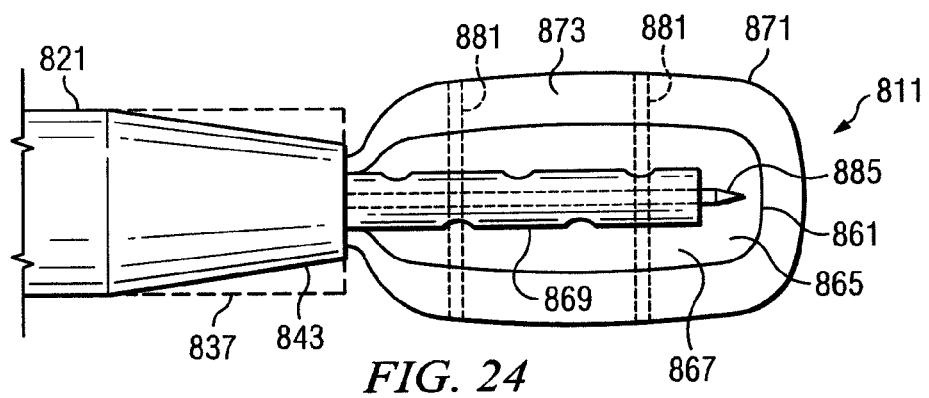
FIG. 24 depicts a front view of the reduced pressure delivery system of FIG. 23, the reduced pressure delivery apparatus being shown outside of the manifold delivery tube but constrained by an impermeable membrane in a relaxed position.
Figure 25:
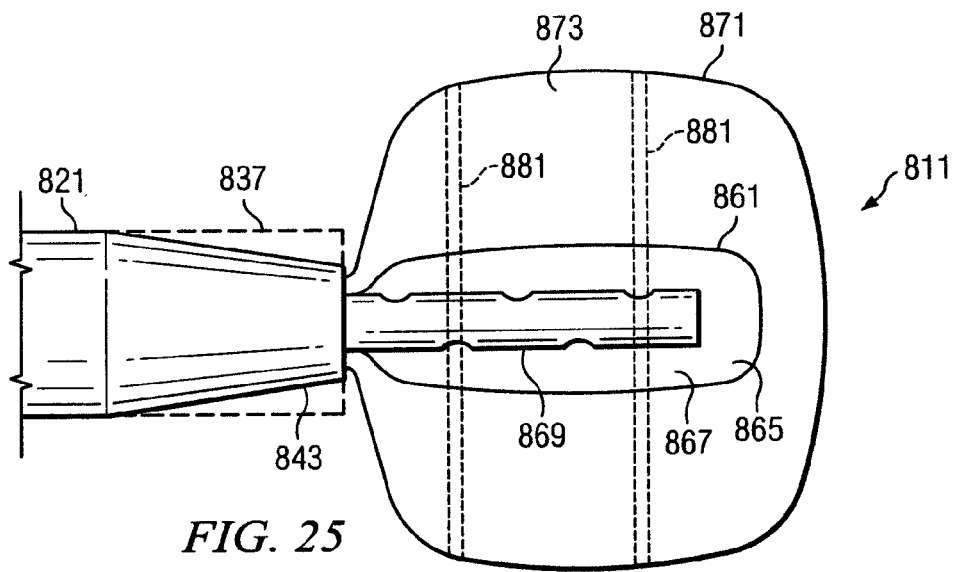
FIG. 25 illustrates a front view of the reduced pressure delivery system of FIG. 23, the reduced pressure delivery apparatus being shown outside of the manifold delivery tube but constrained by an impermeable membrane in an expanded position.

Referring to FIGS. 23-25, a reduced pressure delivery system 811 according to an embodiment of the present invention includes a manifold delivery tube 821 having a tapered distal end 843 that is configured to flex radially outward to an open position such that the inner diameter of the distal end 843 would be substantially the same as or greater than the inner diameter at other portions of the tube 821. The open position of the distal end 843 is schematically illustrated in FIGS. 23-25 by broken lines 837.

The manifold delivery tube 821 further includes a passageway in which a reduced pressure delivery apparatus 861 similar to the other reduced pressure delivery apparatuses described herein is contained. The reduced pressure delivery apparatus 861 includes a flexible barrier 865 and/or a cellular material 867 that is preferably rolled, folded, or otherwise compressed around a reduced pressure delivery tube 869 to reduce the cross-sectional area of the reduced pressure delivery apparatus 861 within the passageway.

An impermeable membrane 871 having an inner space 873 is disposed around the reduced pressure delivery apparatus 861 such that the reduced pressure delivery apparatus 861 is contained within the inner space 873 of the impermeable membrane 871. The impermeable membrane 871 may be a balloon, a sheath, or any other type of membrane that is capable of preventing fluid transmission such that the impermeable membrane 871 can assume at least one of a compressed position (see FIG. 23), a relaxed position (see FIG. 24), and an expanded position (see FIGS. 25 and 25A). The impermeable membrane 871 may be sealingly connected to the manifold delivery tube 821 such that the inner space 873 of the impermeable membrane 871 is in fluid communication with the passageway of the manifold delivery tube 821. The impermeable membrane 871 may alternatively be attached to the reduced pressure delivery tube 869 such that the inner space 873 of the impermeable membrane 871 is in fluid communication with the passageway of the reduced pressure delivery tube 869. The impermeable membrane 871 instead may be attached to a separate control tube or control lumen (see for example FIG. 25A) that fluidly communicates with the inner space 873.

In one embodiment, the impermeable membrane 871 may be provided to further reduce the cross-sectional area of the reduced pressure delivery apparatus 861 within the passageway. To accomplish this, a pressure is applied to the inner space 873 of the impermeable membrane 871 that is less than the ambient pressure surrounding the impermeable membrane 871. A significant portion of the air or other fluid within the inner space 873 is thereby evacuated, placing the impermeable membrane 871 in the compressed position illustrated in FIG. 23. In the compressed position, the impermeable membrane 871 is drawn inward such that a compressive force is applied to the reduced pressure delivery apparatus 861 to further reduce the cross-sectional area of the reduced pressure delivery apparatus 861. As previously described with reference to FIGS. 21 and 22, the reduced pressure delivery apparatus 861 may be delivered to the tissue site following the placement of the distal end 843 of the manifold delivery tube 821 at the tissue site. Placement and manipulation of the impermeable membrane 871 and the reduced pressure delivery apparatus 861 may be accomplished by using endoscopy, ultrasound, fluoroscopy, auscultation, palpation, or any other suitable localization technique. The impermeable membrane 871 may include radio-opaque markers 881 that improve visualization of the impermeable membrane 871 under fluoroscopy prior to its removal.

After pushing the reduced pressure delivery apparatus 861 through the distal end 843, the reduced pressure applied to the inner space 873 may be eased to place the impermeable membrane 871 in the relaxed position (see FIG. 24), thereby facilitating easier removal of the reduced pressure delivery apparatus 861 from the impermeable membrane 871. A removal instrument 885 such as a trocar, stylet, or other sharp instrument may be provided to rupture the impermeable membrane 871. Preferably, the removal instrument 885 is inserted through the reduced pressure delivery tube 869 and is capable of being advanced into contact with the impermeable membrane 871. After rupture of the impermeable membrane 871, the removal instrument 885 and the impermeable membrane 871 may be withdrawn through the manifold delivery tube 821, allowing the flexible barrier 865 and/or cellular material 867 of the reduced pressure delivery apparatus 861 to unroll, unfold, or decompress such that the reduced pressure delivery apparatus 861 can be placed in contact with the tissue site. The unrolling of the flexible barrier 865 and/or cellular material 867 may occur automatically following the relaxation of reduced pressure to the inner space 873 and the removal of the impermeable membrane 871. In some cases, a positive pressure may be delivered through the reduced pressure delivery tube 869 to assist in unrolling or decompressing the flexible barrier 865 and/or cellular material 867. Following final placement of the reduced pressure delivery apparatus 861, the manifold delivery tube 821 is preferably removed from the patient, but the reduced pressure delivery tube 869 associated with the reduced pressure delivery apparatus 861 remains in situ to allow percutaneous application of reduced pressure to the tissue site.

The impermeable membrane 871 may also be used to dissect tissue adjacent the tissue site prior to placing the reduced pressure delivery apparatus 861 against the tissue site. After pushing the reduced pressure delivery apparatus 861 and intact impermeable membrane 871 through the distal end 843 of the manifold delivery tube 821, air or another fluid may be injected or pumped into the inner space 873 of the impermeable membrane 871. A liquid is preferably used to inflate the impermeable membrane 871 since the incompressibility of liquids allow the impermeable membrane 871 to expand more evenly and consistently. The impermeable membrane 871 may expand radially as illustrated in FIG. 25 or directionally depending on its method of manufacture and attachment to the manifold delivery tube 821. As the impermeable membrane 871 expands outward into the expanded position (see FIG. 25) due to the pressure of the air or fluid, a void is dissected adjacent the tissue site. When the void is large enough, the liquid, air or other fluid may be released from the inner space 873 to allow the impermeable membrane 871 to assume the relaxed position. The impermeable membrane 871 may then be ruptured as previously explained and the reduced pressure delivery apparatus 861 inserted adjacent the tissue site.

Figure 25A:
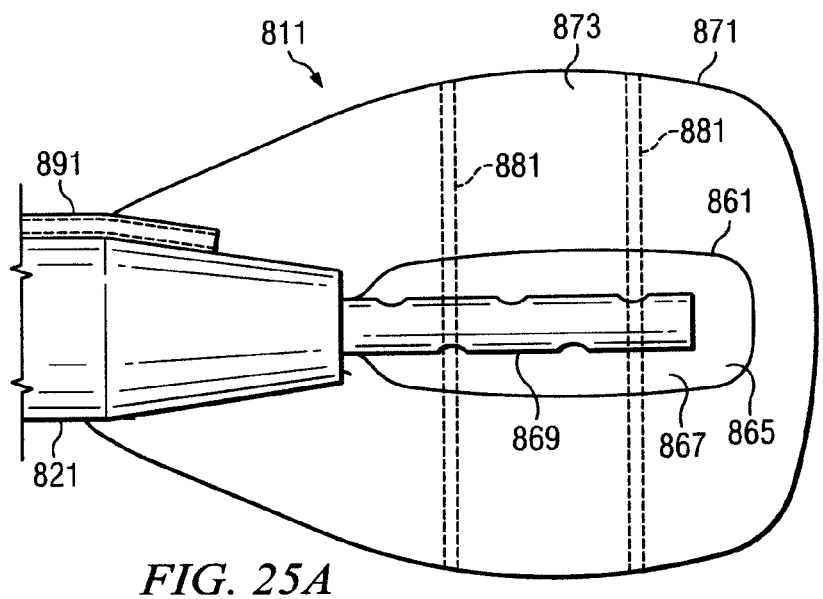
FIG. 25A illustrates a front view of the reduced pressure delivery system of FIG. 23, the reduced pressure delivery apparatus being shown outside of the manifold delivery tube but surrounded by an impermeable membrane in an expanded position.

Referring to FIG. 25A, if the impermeable membrane 871 is used primarily to dissect tissue adjacent the tissue site, the impermeable membrane 871 may be sealingly attached to the manifold delivery tube 821 such that the inner space 873 fluidly communicates with a secondary lumen or tube 891 associated with or attached to the manifold delivery tube 821. The secondary lumen 891 may be used to deliver a liquid, air, or other fluid to the inner space 873 to place the impermeable membrane 871 in the expanded position. Following dissection, the impermeable membrane 871 may be relaxed and ruptured as previously described with reference to FIG. 24.

Figure 26:
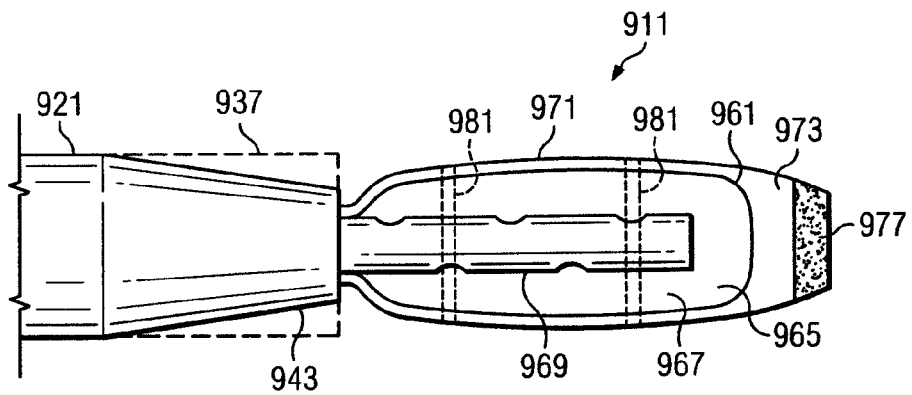
FIG. 26 depicts a front view of a reduced pressure delivery system according to an embodiment of the present invention, the reduced pressure delivery system having a manifold delivery tube that is used to percutaneously insert a reduced pressure delivery apparatus to a tissue site, the reduced pressure delivery apparatus being shown outside of the manifold delivery tube but constrained by an impermeable membrane having a glue seal.

Referring to FIG. 26, a reduced pressure delivery system 911 according to an embodiment of the present invention includes a manifold delivery tube 921 having a tapered distal end 943 that is configured to flex radially outward to an open position such that the inner diameter of the distal end 943 would be substantially the same as or greater than the inner diameter at other portions of the tube 921. The open position of the distal end 943 is schematically illustrated in FIG. 26 by broken lines 937.

The manifold delivery tube 921 further includes a passageway in which a reduced pressure delivery apparatus 961 similar to the other reduced pressure delivery apparatuses described herein is contained. The reduced pressure delivery apparatus 961 includes a flexible barrier 965 and/or a cellular material 967 that is preferably rolled, folded, or otherwise compressed around a reduced pressure delivery tube 969 to reduce the cross-sectional area of the reduced pressure delivery apparatus 961 within the passageway of the manifold delivery tube 921.

An impermeable membrane 971 having an inner space 973 is disposed around the reduced pressure delivery apparatus 961 such that the reduced pressure delivery apparatus 961 is contained within the inner space 973 of the impermeable membrane 971. The impermeable membrane 971 includes a glue seal 977 on one end of the impermeable membrane 971 to provide an alternative method of removing the reduced pressure delivery apparatus 961 from the impermeable membrane 971. The impermeable membrane 971 may be sealingly connected at another end to the manifold delivery tube 921 such that the inner space 973 of the impermeable membrane 971 is in fluid communication with the passageway of the manifold delivery tube 921. Alternatively, the impermeable membrane 971 may be attached to a separate control tube (not shown) that fluidly communicates with the inner space 973.

Similar to the impermeable membrane 871 of FIG. 23, impermeable membrane 971 may be capable of preventing fluid transmission such that the impermeable membrane 971 can assume at least one of a compressed position, a relaxed position, and an expanded position. Since the procedures for placing the impermeable membrane 971 in a compressed position and an expanded position are similar to those for impermeable membrane 871, only the differing process of removing the reduced pressure delivery apparatus 961 is described.

The reduced pressure delivery apparatus 961 is delivered to the tissue site within the impermeable membrane 971 and then properly positioned using endoscopy, ultrasound, fluoroscopy, auscultation, palpation, or any other suitable localization technique. The impermeable membrane 971 may include radio-opaque markers 981 that improve visualization of the impermeable membrane 971 under fluoroscopy prior to its removal. The reduced pressure delivery apparatus 961 is then pushed through the distal end 943 of the manifold delivery tube 921. The reduced pressure applied to the inner space 973 may be eased to place the impermeable membrane 971 in the relaxed position. The reduced pressure delivery apparatus 961 is then pushed through the glue seal 977 to exit the impermeable membrane 971.

Figure 26A:
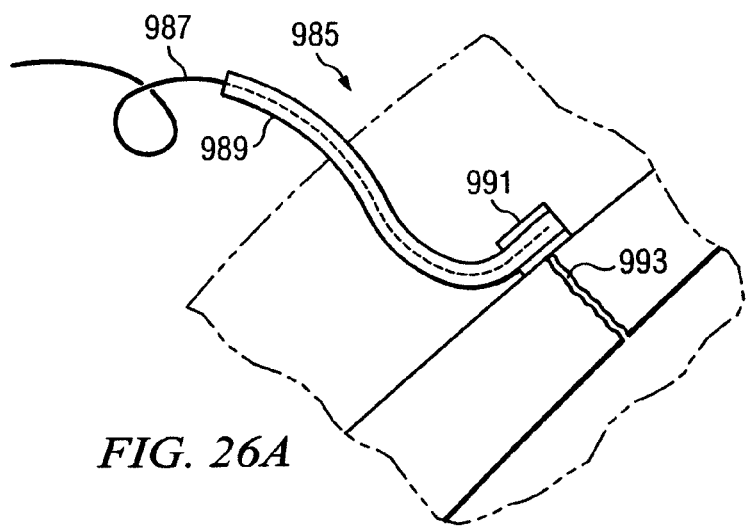
FIG. 26A depicts a front view of a reduced pressure delivery system according to an embodiment of the present invention.

Referring to FIG. 26A, a reduced pressure delivery system 985 according to an embodiment of the present invention may not include a manifold delivery tube similar to manifold delivery tube 921 of FIG. 26. Instead, the reduced pressure delivery system 985 may include a guide wire 987, a reduced pressure delivery tube 989, and a reduced pressure delivery apparatus 991. The reduced pressure delivery apparatus 991 includes a plurality flow channels that is fluidly connected to the reduced pressure delivery tube 989. Instead of using an independent manifold delivery tube to deliver the reduced pressure delivery apparatus 991, the reduced pressure delivery apparatus 991 and reduced pressure delivery tube 989 are placed on the guide wire 987, which is percutaneously guided to a tissue site 993. Preferably, the guide wire 987 and reduced pressure delivery tube 989 penetrate the skin of the patient through a sterile sheath. By guiding the reduced pressure delivery tube 989 and reduced pressure delivery apparatus 991 along the guide wire 987, the reduced pressure delivery apparatus 991 may be placed at the tissue site 993 to allow percutaneous application of reduced pressure tissue treatment.

Since the reduced pressure delivery apparatus 991 is not constrained within a manifold delivery tube during delivery to the tissue site 993, it is preferable to hold the reduced pressure delivery apparatus 991 in a compressed position during delivery. If an elastic foam is used as the reduced pressure delivery apparatus 991, a biocompatible, soluble adhesive may be applied to the foam and the foam compressed. Upon arrival at the tissue site, bodily fluids or other fluids delivered through the reduced pressure delivery tube 989 dissolve the adhesive, allowing the foam to expand into contact with the tissue site. Alternatively, the reduced pressure delivery apparatus 991 may be formed from a compressed, dry hydrogel. The hydrogel absorbs moisture following delivery to the tissue site 993 allowing expansion of the reduced pressure delivery apparatus 991. Still another reduced pressure delivery apparatus 991 may be made from a thermoactive material (e.g. polyethylene glycol) that expands at the tissue site 993 when exposed to the body heat of the patient. In still another embodiment, a compressed reduced pressure delivery apparatus 991 may be delivered to the tissue site 993 in a dissolvable membrane.

Figure 27:
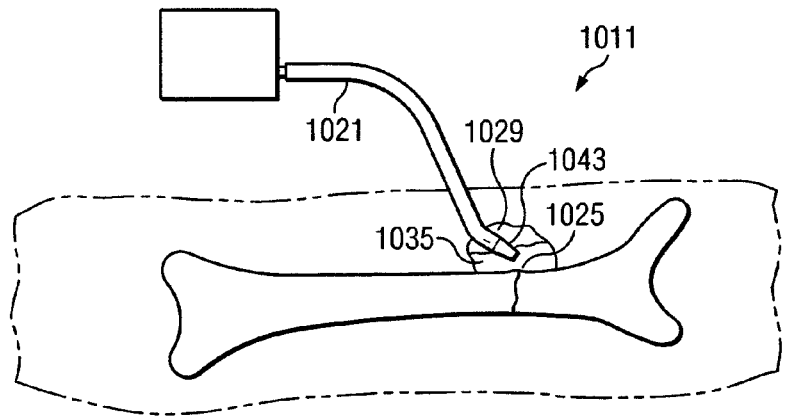
FIG. 27 illustrates a front view of a reduced pressure delivery system according to an embodiment of the present invention, the reduced pressure delivery system having a manifold delivery tube that is used to percutaneously inject a reduced pressure delivery apparatus to a tissue site.

Referring to FIG. 27, a reduced pressure delivery system 1011 according to an embodiment of the present invention includes a manifold delivery tube 1021 having a distal end 1043 that is inserted through a tissue of a patient to access a tissue site 1025. The tissue site 1025 may include a void 1029 that is associated with a wound or other defect, or alternatively a void may be created by dissection, including the dissection techniques described herein.

Following placement of the distal end 1043 within the void 1029 adjacent the tissue site 1025, an injectable, pourable, or flowable reduced pressure delivery apparatus 1035 is delivered through the manifold delivery tube 1021 to the tissue site 1025. The reduced pressure delivery apparatus 1035 preferably exists in a flowable state during delivery to the tissue site, and then, after arrival forms a plurality of flow channels for distribution of reduced pressure or fluids. In some cases, the flowable material may harden into a solid state after arrival at the tissue site, either through a drying process, a curing process, or other chemical or physical reaction. In other cases, the flowable material may form a foam in-situ following delivery to the tissue site. Still other materials may exist in a gel-like state at the tissue site 1025 but still have a plurality of flow channels for delivering reduced pressure. The amount of reduced pressure delivery apparatus 1035 delivered to the tissue site 1025 may be enough to partially or completely fill the void 1029. The reduced pressure delivery apparatus 1035 may include aspects of both a manifold and a scaffold. As a manifold, the reduced pressure delivery apparatus 1035 includes a plurality of pores or open cells that may be formed in the material after delivery to the void 1029. The pores or open cells communicate with one another, thereby creating a plurality of flow channels. The flow channels are used to apply and distribute reduced pressure to the tissue site 1025. As a scaffold, the reduced pressure delivery apparatus 1035 is bioresorbable and serves as a substrate upon and within which new tissue may grow.

In one embodiment, the reduced pressure delivery apparatus 1035 may include poragens such as NaCl or other salts that are distributed throughout a liquid or viscous gel. After the liquid or viscous gel is delivered to the tissue site 1025, the material conforms to the void 1029 and then cures into a solid mass. The water-soluble NaCl poragens dissolve in the presence of bodily fluids leaving a structure with interconnected pores, or flow channels. Reduced pressure and/or fluid is delivered to the flow channels. As new tissue develops, the tissue grows into the pores of the reduced pressure delivery apparatus 1035, and then ultimately replaces the reduced pressure delivery apparatus 1035 as it degrades. In this particular example, the reduced pressure delivery apparatus 1035 serves not only as a manifold, but also as a scaffold for new tissue growth.

In another embodiment, the reduced pressure delivery apparatus 1035 is an alginate mixed with 400 μM mannose beads. The poragens or beads may be dissolved by local body fluids or by irrigational or other fluids delivered to the reduced pressure delivery apparatus 1035 at the tissue site. Following dissolution of the poragens or beads, the spaces previously occupied by the poragens or beads become voids that are interconnected with other voids to form the flow channels within the reduced pressure delivery apparatus 1035.

The use of poragens to create flow channels in a material is effective, but it also forms pores and flow channels that are limited in size to approximately the particle size of the selected poragen. Instead of poragens, a chemical reaction may be used to create larger pores due to the formation of gaseous by-products. For example, in one embodiment, a flowable material may be delivered to the tissue site 1025 that contains sodium bicarbonate and citric acid particles (non-stoichiometric amounts may be used). As the flowable material forms a foam or solid in-situ, bodily fluids will initiate an acid-base reaction between the sodium bicarbonate and the citric acid. The resulting carbon dioxide gas particles that are produced create larger pore and flow channels throughout the reduced pressure delivery apparatus 1035 than techniques relying on poragen dissolution.

The transformation of the reduced pressure delivery apparatus 1035 from a liquid or viscous gel into a solid or a foam can be triggered by pH, temperature, light, or a reaction with bodily fluids, chemicals or other substances delivered to the tissue site. The transformation may also occur by mixing multiple reactive components. In one embodiment, the reduced pressure delivery apparatus 1035 is prepared by selecting bioresorbable microspheres made from any bioresorbable polymer. The microspheres are dispersed in a solution containing a photoinitiator and a hydrogel-forming material such as hyaluronic acid, collagen, or polyethylene glycol with photoreactive groups. The microsphere-gel mixture is exposed to light for a brief period of time to partially crosslink the hydrogel and immobilize the hydrogel on the microspheres. The excess solution is drained, and the microspheres are then dried. The microspheres are delivered to the tissue site by injection or pouring, and following delivery, the mixture absorbs moisture, and the hydrogel coating becomes hydrated. The mixture is then again exposed to light, which crosslinks the microspheres, creating a plurality of flow channels. The crosslinked microspheres then serve as a manifold to deliver reduced pressure to the tissue site and as a porous scaffold to promote new tissue growth.

In addition to the preceding embodiments described herein, the reduced pressure delivery apparatus 1035 may be made from a variety of materials, including without limitation calcium phosphate, collagen, alginate, cellulose, or any other equivalent material that is capable of being delivered to the tissue site as a gas, liquid, gel, paste, putty, slurry, suspension, or other flowable material and is capable of forming multiple flow paths in fluid communication with the tissue site. The flowable material may further include particulate solids, such as beads, that are capable of flowing through the manifold delivery tube 1021 if the particulate solids are sufficiently small in size. Materials that are delivered to the tissue site in a flowable state may polymerize or gel in-situ.

Figure 27A:
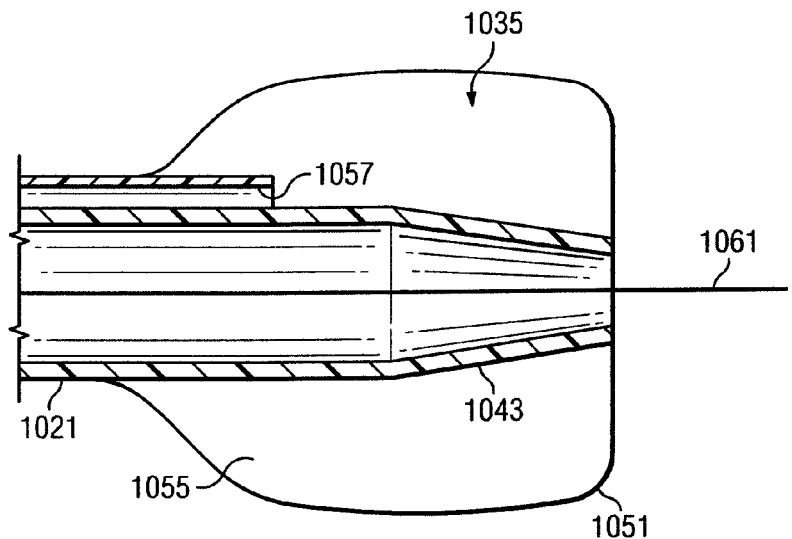
FIG. 27A illustrates a front view of a reduced pressure delivery system according to an embodiment of the present invention, the reduced pressure delivery system having a manifold delivery tube that is used to percutaneously deliver a reduced pressure delivery apparatus to an impermeable membrane positioned at a tissue site.

As previously described, the reduced pressure delivery apparatus 1035 may injected or poured directly into the void 1029 adjacent the tissue site 1025. Referring to FIG. 27A, the manifold delivery tube 1021 may include an impermeable or semi-permeable membrane 1051 at the distal end 1043 of the manifold delivery tube 1021. The membrane 1051 includes an inner space 1055 that fluidly communicates with a secondary lumen 1057 attached to the manifold delivery tube 1021. The manifold delivery tube 1021 is guided to the tissue site 1025 over a guide wire 1061.

The reduced pressure delivery apparatus 1035 may be injected or poured through the secondary lumen 1057 to fill the inner space 1055 of the membrane 1051. As the fluid or gel fills the membrane 1051, the membrane 1051 expands to fill the void 1029 such that the membrane is in contact with the tissue site 1025. As the membrane 1051 expands, the membrane 1051 may be used to dissect additional tissue adjacent or near the tissue site 1025. The membrane 1051, if impermeable, may be physically ruptured and removed, leaving behind the reduced pressure delivery apparatus 1035 in contact with the tissue site 1025. Alternatively, the membrane 1051 may be made from a dissolvable material that dissolves in the presence of bodily fluids or biocompatible solvents that may be delivered to the membrane 1051. If the membrane 1051 is semi-permeable, the membrane 1051 may remain in situ. The semi-permeable membrane 1051 allows communication of reduced pressure and possibly other fluids to the tissue site 1025.

Figure 28:
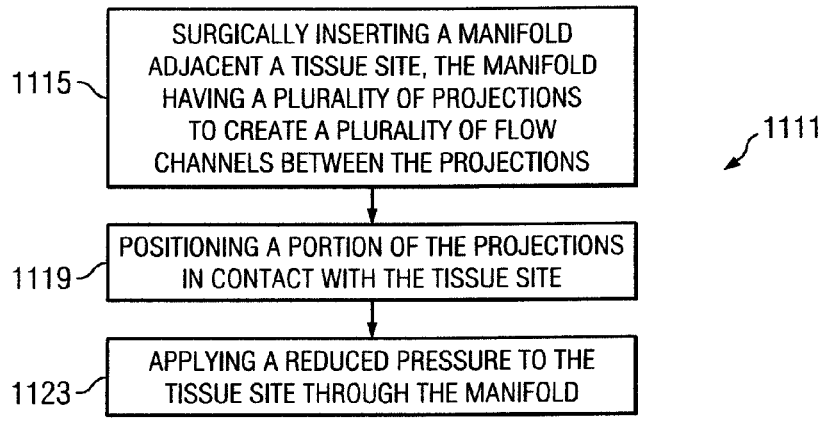
FIG. 28 depicts a flow chart of a method of administering a reduced pressure tissue treatment to a tissue site according to an embodiment of the present invention.

Referring to FIG. 28, a method 1111 of administering a reduced pressure tissue treatment to a tissue site includes at 1115 surgically inserting a manifold adjacent the tissue site, the manifold having a plurality of projections extending from a flexible barrier to create a plurality of flow channels between the projections. The manifold is positioned at 1119 such that at least a portion of the projections are in contact with the tissue site. At 1123, a reduced pressure is applied through the manifold to the tissue site.

Figure 29:
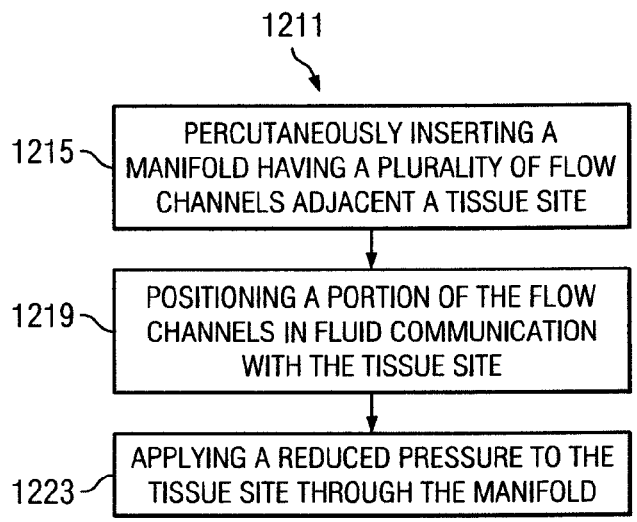
FIG. 29 illustrates a flow chart of a method of administering a reduced pressure tissue treatment to a tissue site according to an embodiment of the present invention.

Referring to FIG. 29, a method 1211 of administering a reduced pressure tissue treatment to a tissue site includes at 1215 percutaneously inserting a manifold adjacent the tissue site. The manifold may include a plurality of projections extending from a flexible barrier to create a plurality of flow channels between the projections. Alternatively, the manifold may include cellular material having a plurality of flow channels within the cellular material. Alternatively, the manifold may be formed from an injectable or pourable material that is delivered to the tissue site and forms a plurality of flow channels after arriving at the tissue site. At 1219, the manifold is positioned such that at a least a portion of the flow channels are in fluid communication with the tissue site. A reduced pressure is applied to the tissue site through the manifold at 1223.

Figure 30:
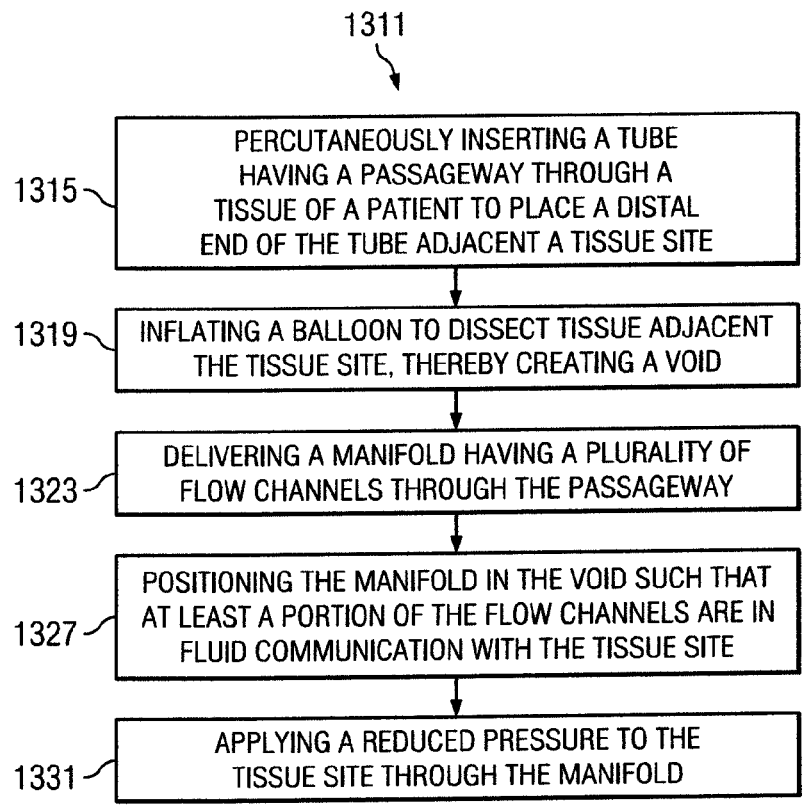
FIG. 30 depicts a flow chart of a method of administering a reduced pressure tissue treatment to a tissue site according to an embodiment of the present invention.

Referring to FIG. 30, a method 1311 of administering a reduced pressure tissue treatment to a tissue site includes at 1315 percutaneously inserting a tube having a passageway through a tissue of a patient to place a distal end of the tube adjacent the tissue site. At 1319, a balloon associated with the tube may be inflated to dissect tissue adjacent the tissue site, thereby creating a void. At 1323, a manifold is delivered through the passageway. The manifold may include a plurality of projections extending from a flexible barrier to create a plurality of flow channels between the projections. Alternatively, the manifold may include cellular material having a plurality of flow channels within the cellular material. Alternatively, the manifold may be formed from an injectable or pourable material that is delivered to the tissue site as described previously with reference to FIG. 27. The manifold is positioned in the void at 1327 such that at least a portion of the flow channels are in fluid communication with the tissue site. At 1331, a reduced pressure is applied to the tissue site through the manifold via a reduced pressure delivery tube or any other delivery means.

Figure 31:
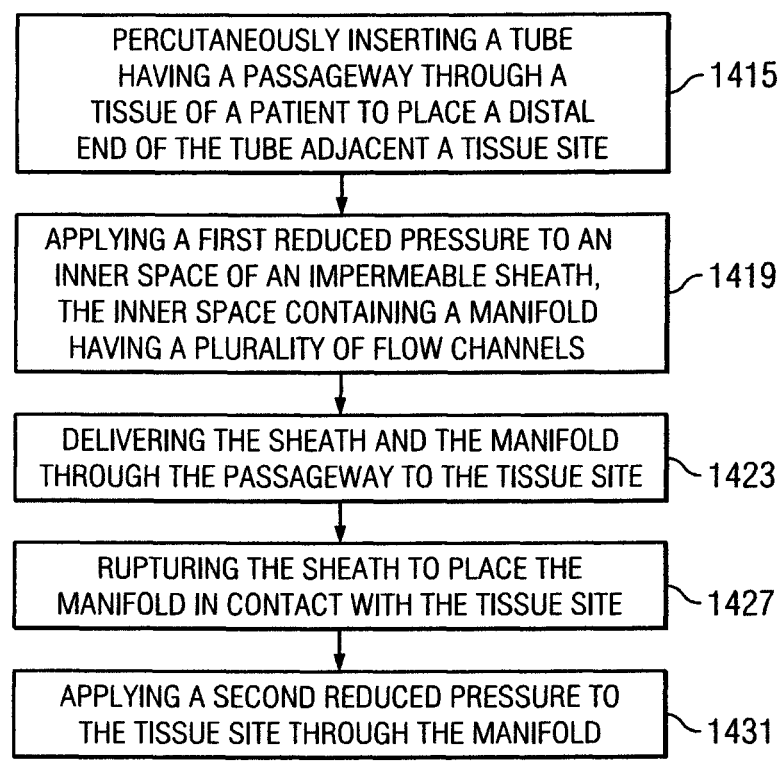
FIG. 31 illustrates a flow chart of a method of administering a reduced pressure tissue treatment to a tissue site according to an embodiment of the present invention.

Referring to FIG. 31, a method 1411 of administering a reduced pressure tissue treatment to a tissue site includes at 1415 percutaneously inserting a tube having a passageway through a tissue of a patient to place a distal end of the tube adjacent the tissue site. At 1423, a manifold is delivered through the passageway to the tissue site within an impermeable sheath, the impermeable sheath at 1419 having been subjected to a first reduced pressure less than an ambient pressure of the sheath. At 1427, the sheath is ruptured to place the manifold in contact with the tissue site. At 1431, a second reduced pressure is applied through the manifold to the tissue site.

Referring to FIGS. 32 and 33, a reduced pressure delivery apparatus 1511 according to an embodiment of the present invention includes an orthopedic hip prosthesis 1515 for replacing the existing femoral head of a femur 1517 of a patient. The hip prosthesis 1515 includes a stem portion 1521 and a head portion 1525. The stem portion 1521 is elongated for insertion within a passage 1529 reamed in a shaft of the femur 1517. A porous coating 1535 is disposed around the stem portion and preferably is constructed from sintered or vitrified ceramics or metal. Alternatively, a cellular material having porous characteristic could be disposed around the stem portion. A plurality of flow channels 1541 is disposed within the stem portion 1521 of the hip prosthesis 1515 such that the flow channels 1541 are in fluid communication with the porous coating 1535. A connection port 1545 is fluidly connected to the flow channels 1541, the port being configured for releasable connection to a reduced pressure delivery tube 1551 and a reduced pressure delivery source 1553. The flow channels 1541 are used to deliver a reduced pressure to the porous coating 1535 and/or the bone surrounding the hip prosthesis 1515 following implantation. The flow channels 1541 may include a main feeder line 1543 that fluidly communicates with several lateral branch lines 1547, which communicate with the porous coating 1535. The lateral branch lines 1545 may be oriented normal to the main feeder line 1543 as illustrated in FIG. 32, or may be oriented at angles to the main feeder line 1543. An alternative method for distributing the reduced pressure includes providing a hollow hip prosthesis, and filling the inner space of the prosthesis with a cellular (preferably open-cell) material that is capable of fluidly communicating with the porous coating 1535.

Referring more specifically to FIG. 33, hip prosthesis 1515 may further include a second plurality of flow channels 1561 within the stem portion 1521 to provide a fluid to the porous coating 1535 and/or the bone surrounding the hip prosthesis 1515. The fluid could include filtered air or other gases, antibacterial agents, antiviral agents, cell-growth promotion agents, irrigation fluids, chemically active fluids, or any other fluid. If it is desired to introduce multiple fluids to the bone surrounding the hip prosthesis 1515, additional paths of fluid communication may be provided. A connection port 1565 is fluidly connected to the flow channels 1561, the port 1565 being configured for releasable connection to a fluid delivery tube 1571 and a fluid delivery source 1573. The flow channels 1561 may include a main feeder line 1583 that fluidly communicates with several lateral branch lines 1585, which communicate with the porous coating 1535. The lateral branch lines 1585 may be oriented normal to the main feeder line 1583 as illustrated in FIG. 33, or may be oriented at angles to the main feeder line 1583.

The delivery of reduced pressure to the first plurality of flow channels 1541 and the delivery of the fluid to the second plurality of flow channels 1561 may be accomplished by separate tubes such as reduced pressure delivery tube 1551 and fluid delivery tube 1571. Alternatively, a tube having multiple lumens as described previously herein may be used to separate the communication paths for delivering the reduced pressure and the fluid. It should further be noted that while it is preferred to provide separate paths of fluid communication within the hip prosthesis 1515, the first plurality of flow channels 1541 could be used to deliver both the reduced pressure and the fluid to the bone surrounding the hip prosthesis 1515.

As previously described, application of reduced pressure to bone tissue promotes and speeds the growth of new bone tissue. By using the hip prosthesis 1515 as a manifold to deliver reduced pressure to the area of bone surrounding the hip prosthesis, recovery of the femur 1517 is faster, and the hip prosthesis 1515 integrates more successfully with the bone. Providing the second plurality of flow channels 1561 to vent the bone surrounding the hip prosthesis 1515 improves the successful generation of new bone around the prosthesis.

Following the application of reduced pressure through the hip prosthesis 1515 for a selected amount of time, the reduced pressure delivery tube 1551 and fluid delivery tube 1571 may be disconnected from the connection ports 1545, 1565 and removed from the patient's body, preferably without a surgically-invasive procedure. The connection between the connection ports 1545, 1565 and the tubes 1551, 1571 may be a manually-releasable connection that is effectuated by applying an axially-oriented tensile force to the tubes 1551, 1571 on the outside of the patient's body. Alternatively, the connection ports 1545, 1565 may be bioresorbable or dissolvable in the presence of selected fluids or chemicals such that release of the tubes 1551, 1571 may be obtained by exposing the connection ports 1545, 1565 to the fluid or chemical. The tubes 1551, 1571 may also be made from a bioresorbable material that dissolves over a period of time or an activated material that dissolves in the presence of a particular chemical or other substance.

The reduced pressure delivery source 1553 may be provided outside the patient's body and connected to the reduced pressure delivery tube 1551 to deliver reduced pressure to the hip prosthesis 1515. Alternatively, the reduced pressure delivery source 1553 may be implanted within the patient's body, either on-board or near the hip prosthesis 1515. Placement of the reduced pressure delivery source 1553 within the patient's body eliminates the need for a percutaneous fluid connection. The implanted reduced pressure delivery source 1553 may be a traditional pump that is operably connected to the flow channels 1541. The pump may be powered by a battery that is implanted within the patient, or may be powered by an external battery that is electrically and percutaneously connected to the pump. The pump may also be driven directly by a chemical reaction that delivers a reduced pressure and circulates fluids through the flow channels 1541, 1561.

While only the stem portion 1521 and head portion 1525 of the hip prosthesis 1515 are illustrated in FIGS. 32 and 33, it should be noted that the flow channels and means for applying reduced pressure tissue treatment described herein could be applied to any component of the hip prosthesis 1515 that contacts bone or other tissue, including for example the acetabular cup.

Figure 34:
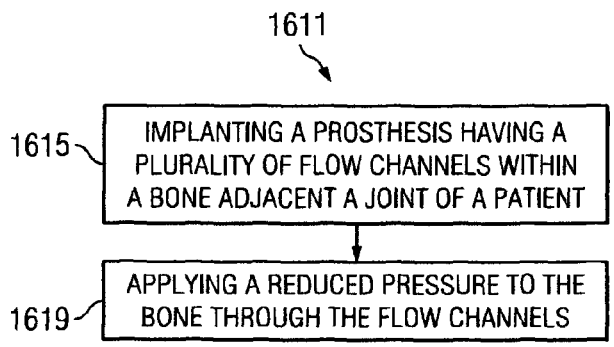
FIG. 34 depicts a flow chart of a method for repairing a joint of a patient using reduced pressure tissue treatment according to an embodiment of the present invention.

Referring to FIG. 34, a method 1611 for repairing a joint of a patient includes at 1615 implanting a prosthesis within a bone adjacent the joint. The prosthesis could be a hip prosthesis as described above or any other prosthesis that assists in restoring mobility to the joint of the patient. The prosthesis includes a plurality of flow channels configured to fluidly communicate with the bone. At 1619, a reduced pressure is applied to the bone through the plurality of flow channels to improve oseointegration of the prosthesis.

Figure 35:
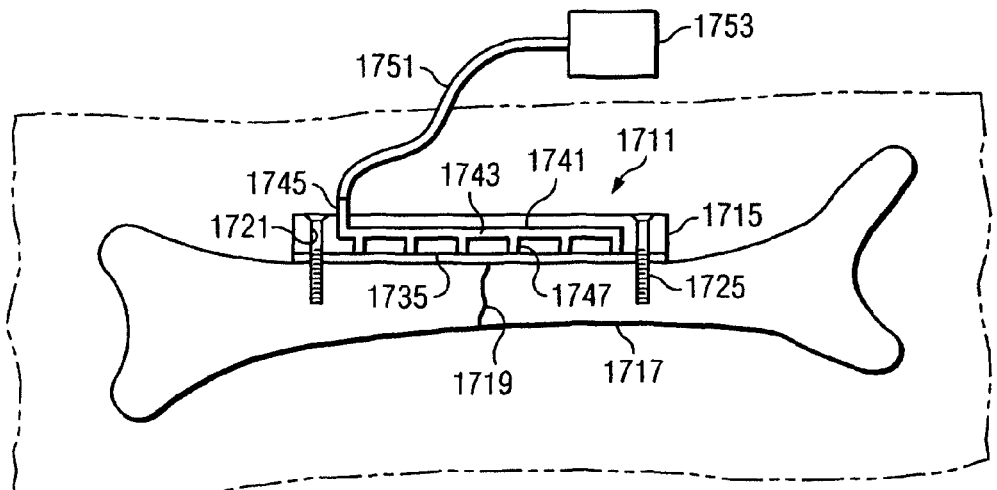
FIG. 35 illustrates a cross-sectional front view of a reduced pressure delivery apparatus according to an embodiment of the present invention, the reduced pressure delivery apparatus including a orthopedic fixation device having a plurality of flow channels for applying a reduced pressure to an area of bone adjacent the orthopedic fixation device.
Figure 36:
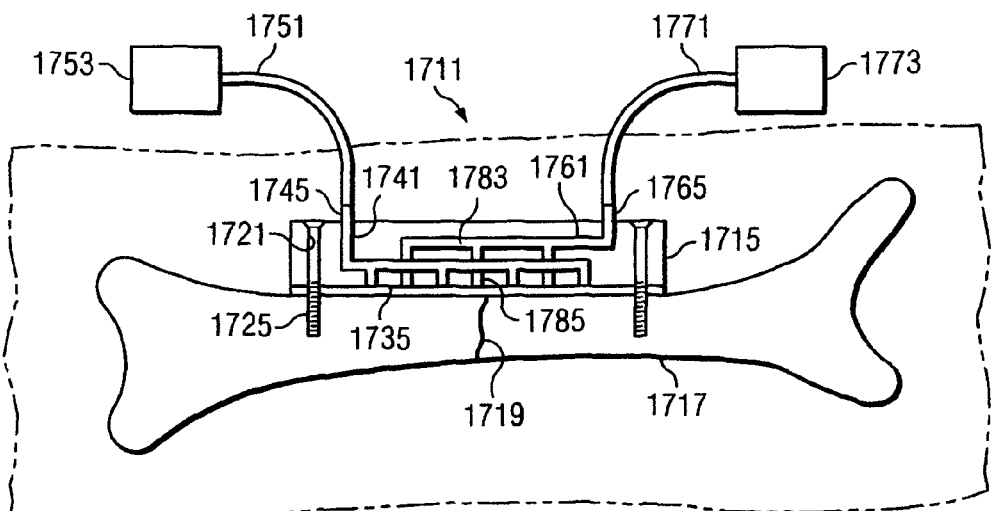
FIG. 36 depicts a cross-sectional front view of the orthopedic fixation device of FIG. 35 having a second plurality of flow channels for delivering a fluid to the area of bone adjacent the orthopedic fixation device.

Referring to FIGS. 35 and 36, a reduced pressure delivery apparatus 1711 according to an embodiment of the present invention includes an orthopedic fixation device 1715 for securing a bone 1717 of a patient that includes a fracture 1719 or other defect. The orthopedic fixation device 1715 illustrated in FIGS. 35 and 36 is a plate having a plurality of passages 1721 for anchoring the orthopedic fixation device 1715 to the bone 1717 with screws 1725, pins, bolts, or other fasteners. A porous coating 1735 may be disposed on a surface of the orthopedic fixation device 1715 that is to contact the bone 1717. The porous coating is preferably constructed from sintered or vitrified ceramics or metal. Alternatively, a cellular material having porous characteristic could be disposed between the bone 1717 and the orthopedic fixation device 1715. A plurality of flow channels 1741 is disposed within the orthopedic fixation device 1715 such that the flow channels 1741 are in fluid communication with the porous coating 1735. A connection port 1745 is fluidly connected to the flow channels 1741, the port being configured for connection to a reduced pressure delivery tube 1751 and a reduced pressure delivery source 1753. The flow channels 1741 are used to deliver a reduced pressure to the porous coating 1735 and/or the bone surrounding the orthopedic fixation device 1715 following fixation of the orthopedic fixation device 1715 to the bone 1717. The flow channels 1741 may include a main feeder line 1743 that fluidly communicates with several lateral branch lines 1747, which communicate with the porous coating 1735. The lateral branch lines 1747 may be oriented normal to the main feeder line 1743 as illustrated in FIG. 35, or may be oriented at angles to the main feeder line 1743. An alternative method for distributing the reduced pressure includes providing a hollow orthopedic fixation device, and filling the inner space of the orthopedic fixation device with a cellular (preferably open-cell) material that is capable of fluidly communicating with the porous coating 1735.

The orthopedic fixation device 1715 may be a plate as shown in FIG. 35, or alternatively may be a fixation device such as a sleeve, a brace, a strut, or any other device that is used to stabilize a portion of the bone. The orthopedic fixation device 1715 may further be fasteners used to attach prosthetic or other orthopedic devices or implanted tissues (e.g. bone tissues or cartilage), provided that the fasteners include flow channels for delivering reduced pressure to tissue adjacent to or surrounding the fasteners. Examples of these fasteners may include pins, bolts, screws, or any other suitable fastener.

Referring more specifically to FIG. 36, the orthopedic fixation device 1715 may further include a second plurality of flow channels 1761 within the orthopedic fixation device 1715 to provide a fluid to the porous coating 1735 and/or the bone surrounding the orthopedic fixation device 1715. The fluid could include filtered air or other gases, antibacterial agents, antiviral agents, cell-growth promotion agents, irrigation fluids, chemically active agents, or any other fluid. If it is desired to introduce multiple fluids to the bone surrounding the orthopedic fixation device 1715, additional paths of fluid communication may be provided. A connection port 1765 is fluidly connected to the flow channels 1761, the port 1765 being configured for connection to a fluid delivery tube 1771 and a fluid delivery source 1773. The flow channels 1761 may include a main feeder line 1783 that fluidly communicates with several lateral branch lines 1785, which communicate with the porous coating 1735. The lateral branch lines 1785 may be oriented normal to the main feeder line 1783 as illustrated in FIG. 33, or may be oriented at angles to the main feeder line 1783.

The delivery of reduced pressure to the first plurality of flow channels 1741 and the delivery of the fluid to the second plurality of flow channels 1761 may be accomplished by separate tubes such as reduced pressure delivery tube 1751 and fluid delivery tube 1771. Alternatively, a tube having multiple lumens as described previously herein may be used to separate the communication paths for delivering the reduced pressure and the fluid. It should further be noted that while it is preferred to provide separate paths of fluid communication within the orthopedic fixation device 1715, the first plurality of flow channels 1741 could be used to deliver both the reduced pressure and the fluid to the bone adjacent the orthopedic fixation device 1715.

The use of orthopedic fixation device 1715 as a manifold to deliver reduced pressure to the area of bone adjacent the orthopedic fixation device 1715 speeds and improves recovery of the defect 1719 of the bone 1717. Providing the second plurality of flow channels 1761 to communicate fluids to the bone surrounding the orthopedic fixation device 1715 improves the successful generation of new bone near the orthopedic fixation device.

Figure 37:
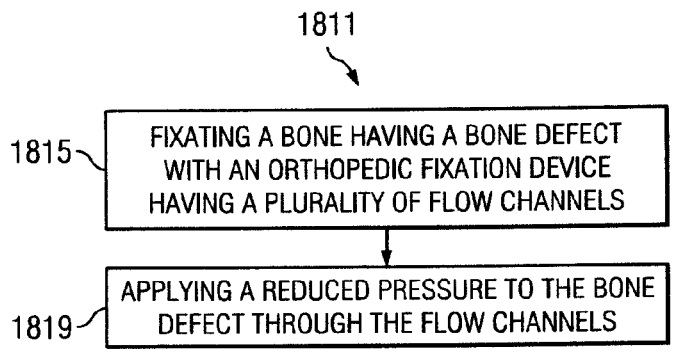
FIG. 37 illustrates a flow chart of a method for healing a bone defect of a bone using reduced pressure tissue treatment according to an embodiment of the present invention.

Referring to FIG. 37, a method 1811 for healing a bone defect of a bone includes at 1815 fixating the bone using an orthopedic fixation device. The orthopedic fixation device includes a plurality of flow channels disposed within the orthopedic fixation device. At 1819, a reduced pressure is applied to the bone defect through the plurality of flow channels.

Figure 38:
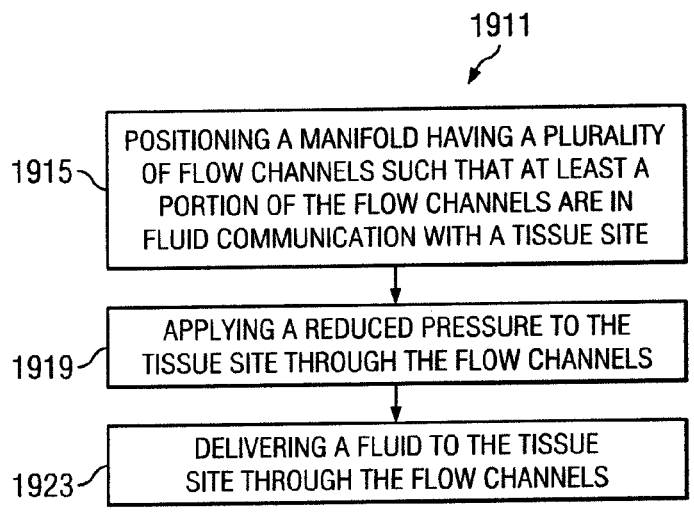
FIG. 38 depicts a flow chart of a method of administering a reduced pressure tissue treatment to a tissue site according to an embodiment of the present invention.

Referring to FIG. 38, a method 1911 for administering reduced pressure tissue treatment to a tissue site includes at 1915 positioning a manifold having a plurality of flow channels such that at least a portion of the flow channels are in fluid communication with the tissue site. A reduced pressure is applied at 1919 to the tissue site through the flow channels, and a fluid is delivered at 1923 to the tissue site through the flow channels.

Figure 39:
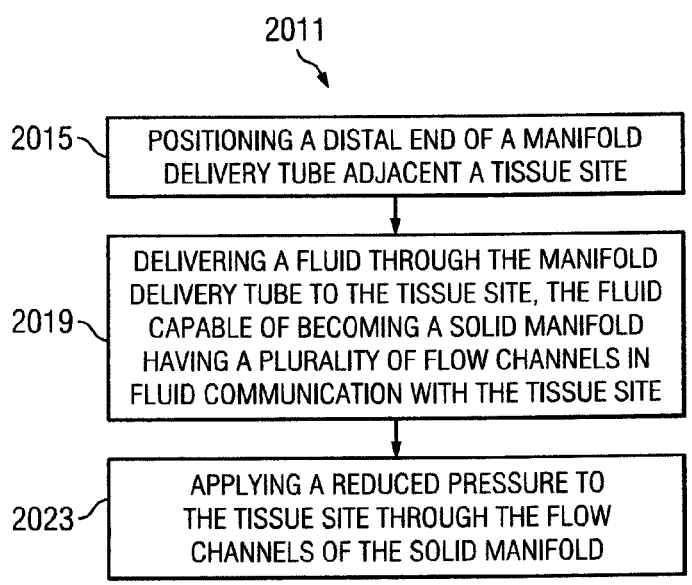
FIG. 39 illustrates a flow chart of a method of administering a reduced pressure tissue treatment to a tissue site according to an embodiment of the present invention.

Referring to FIG. 39, a method 2011 for administering reduced pressure tissue treatment to a tissue site includes at 2015 positioning a distal end of a manifold delivery tube adjacent the tissue site. At 2019 a fluid is delivered through the manifold delivery tube to the tissue site. The fluid is capable of filling a void adjacent the tissue site and becoming a solid manifold having a plurality of flow channels in fluid communication with the tissue site. A reduced pressure is applied at 2023 to the tissue site through the flow channels of the solid manifold.

Referring to FIGS. 40-48, a reduced pressure delivery system 2111 includes a primary manifold 2115 having a flexible wall 2117 surrounding a primary flow passage 2121. The flexible wall 2117 is connected at a proximal end 2123 to a reduced pressure delivery tube 2125. Since the shape of the reduced pressure delivery tube 2125 will typically be round in cross-section, and since the shape of the primary manifold 2115 in cross-section may be other than round (i.e. rectangular in FIGS. 40-45 and triangular in FIGS. 46-48), a transition region 2129 is provided between the reduced pressure delivery tube 2125 and the primary manifold 2115. The primary manifold 2115 may be adhesively connected to the reduced pressure delivery tube 2125, connected using other means such as fusing or insert molding, or alternatively may be integrally connected by co-extrusion. The reduced pressure delivery tube 2125 delivers reduced pressure to the primary manifold 2115 for distribution at or near the tissue site.

A blockage prevention member 2135 is positioned within the primary manifold to prevent collapse of the manifold 2115, and thus blockage of the primary flow passage 2121 during application of reduced pressure. In one embodiment, the blockage prevention member 2135 may be a plurality of projections 2137 (see FIG. 44) disposed on an inner surface 2141 of the flexible wall 2117 and extending into the primary flow passage 2121. In another embodiment, the blockage prevention member 2135 may be a single or multiple ridges 2145 disposed on the inner surface 2141 (see FIGS. 40 and 41). In yet another embodiment, the blockage prevention member 2135 may include a cellular material 2149 disposed within the primary flow passage such as that illustrated in FIG. 47. The blockage prevention member 2135 may be any material or structure that is capable of being inserted within the flow passage or that is capable of being integrally or otherwise attached to the flexible wall 2117. The blockage prevention member 2135 is able to prevent total collapse of the flexible wall 2117, while still allowing the flow of fluids through the primary flow passage 2121.

The flexible wall 2117 further includes a plurality of apertures 2155 through the flexible wall 2117 that communicate with the primary flow passage 2121. The apertures 2155 allow reduced pressure delivered to the primary flow passage 2121 to be distributed to the tissue site. Apertures 2155 may be selectively positioned around the circumference of the manifold 2115 to preferentially direct the delivery of vacuum. For example, in FIG. 51, apertures may be placed facing the bone, facing the overlying tissue, or both.

The reduced pressure delivery tube 2125 preferably includes a first conduit 2161 having at least one outlet fluidly connected to the primary flow passage 2121 to deliver reduced pressure to the primary flow passage 2121. A second conduit 2163 may also be provided to purge the primary flow passage 2121 and the first conduit 2161 with a fluid to prevent or resolve blockages caused by wound exudate and other fluids drawn from the tissue site. The second conduit 2163 preferably includes at least one outlet positioned proximate to at least one of the primary flow passage 2121 and the at least one outlet of the first conduit 2161.

Figure 40:
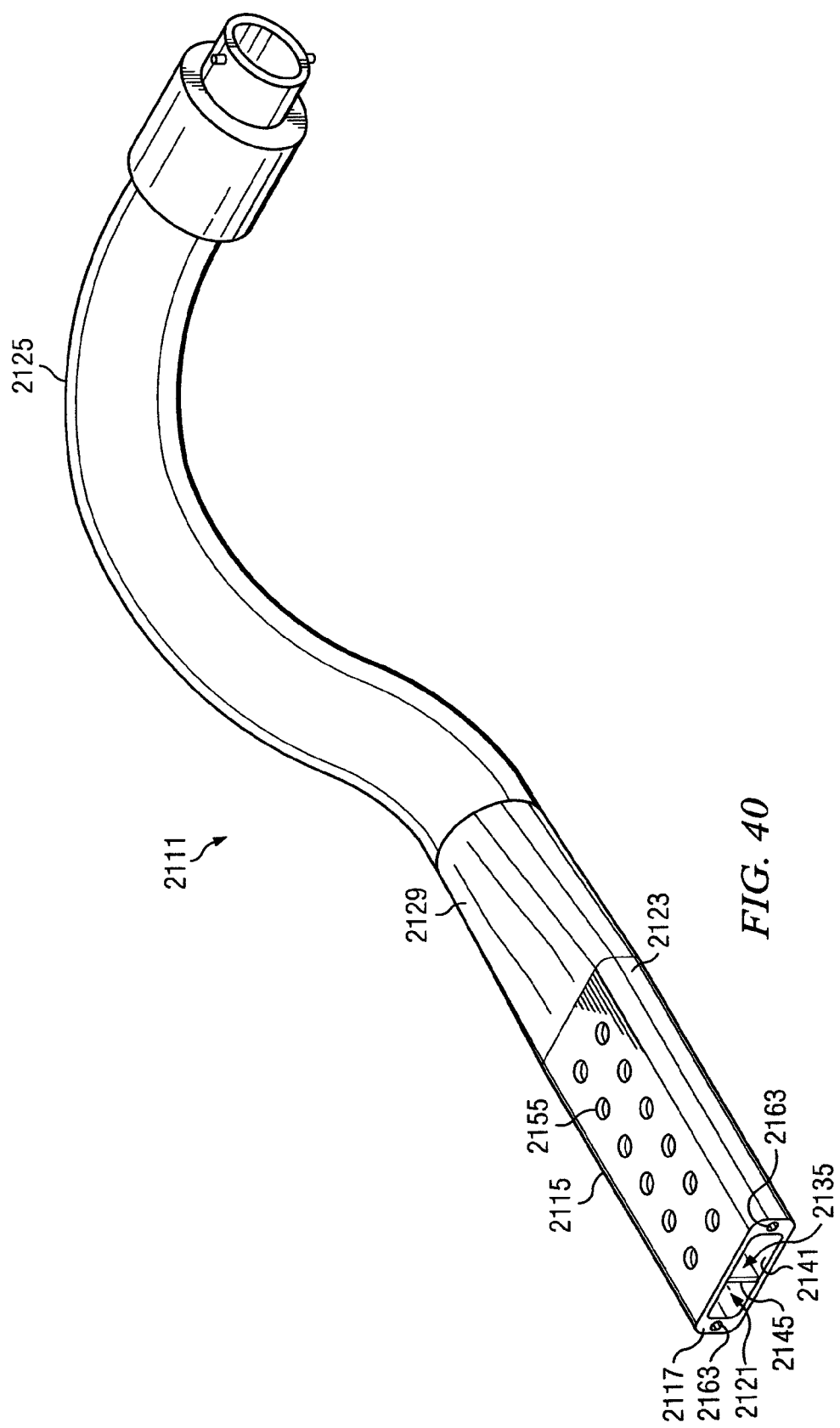

Referring more specifically to FIGS. 40 and 41, the reduced pressure delivery system 2111 the second conduit 2163 may include multiple conduits for purging the primary flow passage 2121 and the first conduit 2161. While the end of the flexible wall 2117 opposite the end attached to reduced pressure delivery tube 2125 may be open as illustrated in FIG. 40, it has been found that capping the end of the flexible wall 2117 may improve the performance and reliability of the purging function. Preferably, a head space 2171 is provided for between the capped end of the flexible wall and the end of the second conduits 2163. The head space 2171 allows for a buildup of purge fluid during the purging process, which helps drive the purge fluid through the primary flow passage 2121 and into the first conduit 2161.

Also illustrated in FIG. 41 is the divider that serves as the blockage prevention member 2135. The centrally-located divider bifurcates the primary flow passage 2121 into two chambers, which allows continued operation of the primary manifold 2115 if one of the chambers becomes blocked and purging is unable to resolve the blockage.

Referring to FIGS. 49 and 50, a reduced pressure delivery system 2211 includes a primary manifold 2215 that is integral to a reduced pressure delivery tube 2217. The reduced pressure delivery tube 2217 includes a central lumen 2223 and a plurality of ancillary lumens 2225. While the ancillary lumens 2225 may used to measure pressure at or near the tissue site, the ancillary lumens 2225 may further be used to purge the central lumen 2223 to prevent or resolve blockages. A plurality of apertures 2231 communicate with the central lumen 2223 to distribute the reduced pressure delivered by the central lumen 2223. As illustrated in FIG. 50, it is preferred that the apertures 2231 not penetrate the ancillary lumens 2225. Also illustrated in FIG. 50 is the countersunk end of the reduced pressure delivery tube, which creates a head space 2241 beyond the end of the ancillary lumens 2225. If tissue, scaffolds, or other materials were to engage the end of the reduced pressure delivery tube 2217 during application of reduced pressure, the head space 2241 would continue to allow purging fluid to be delivered to the central lumen 2223.

In operation, the reduced pressure delivery systems 2111, 2211 of FIGS. 40-50 may be applied directly to a tissue site for distributing reduced pressure to the tissue site. The low-profile shape of the primary manifolds is highly desirous for the percutaneous installation and removal techniques described herein. Similarly, the primary manifolds may also be inserted surgically.

Referring to FIG. 51, the primary manifolds 2115, 2215 may be used in conjunction with a secondary manifold 2321. In FIG. 51, the secondary manifold 2321 includes a two-layered felted mat. The first layer of the secondary manifold 2321 is placed in contact with a bone tissue site that includes a bone fracture. The primary manifold 2115 is placed in contact with the first layer, and the second layer of the secondary manifold 2321 is placed on top of the primary manifold 2115 and first layer. The secondary manifold 2321 allows fluid communication between the primary manifold 2115 and the tissue site, yet prevents direct contact between the tissue site and the primary manifold 2115.

Preferably, the secondary manifold 2321 is bioabsorbable, which allows the secondary manifold 2321 to remain in situ following completion of reduced pressure treatment. Upon completion of reduced pressure treatment, the primary manifold 2115 may be removed from between the layers of the secondary manifold with little or no disturbance to the tissue site. In one embodiment, the primary manifold may be coated with a lubricious material or a hydrogel-forming material to ease removal from between the layers.

The secondary manifold preferably serves as a scaffold for new tissue growth. As a scaffold, the secondary manifold may be comprised of at least one material selected from the group of polylactic acid, polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, calcium phosphate, calcium sulfate, calcium carbonate, bioglass, stainless steel, titanium, tantalum, allografts, and autografts.

The purging function of the reduced pressure delivery systems 2111, 2211 described above may be employed with any of the manifolds described herein. The ability to purge a manifold or a conduit delivering reduced pressure prevents blockages from forming that hinder the administration of reduced pressure. These blockages typically form as the pressure near the tissue site reaches equilibrium and egress of fluids around the tissue site slows. It has been found that purging the manifold and reduced pressure conduit with air for a selected amount of time at a selected interval assists in preventing or resolving blockages.

More specifically, air is delivered through a second conduit separate from a first conduit that delivers reduced pressure. An outlet of the second conduit is preferably proximate to the manifold or an outlet of the first conduit. While the air may be pressurized and "pushed" to the outlet of the second conduit, the air is preferably drawn through the second conduit by the reduced pressure at the tissue site. It has been found that delivery of air for two (2) seconds at intervals of sixty (60) seconds during the application of reduced pressure is sufficient to prevent blockages from forming in many instances. This purging schedule provides enough air to sufficiently move fluids within the manifold and first conduit, while preventing the introduction of too much air. Introducing too much air, or introducing air at too high of an interval frequency will result in the reduced pressure system not being able to return to the target reduced pressure between purge cycles. The selected amount of time for delivering a purging fluid and the selected interval at which the purging fluid is delivered will typically vary based on the design and size of system components (e.g. the pump, tubing, etc.). However, air should be delivered in a quantity and at a frequency that is high enough to sufficiently clear blockages while allowing the full target pressure to recover between purging cycles.

Referring to FIG. 52, in one illustrative embodiment, a reduced pressure delivery system 2411 includes a manifold 2415 fluidly connected to a first conduit 2419 and a second conduit 2423. The first conduit 2419 is connected to a reduced pressure source 2429 to provide reduced pressure to the manifold 2415. The second conduit 2423 includes an outlet 2435 positioned in fluid communication with the manifold 2415 and proximate an outlet of the first conduit 2419. The second conduit 2423 is fluidly connected to a valve 2439, which is capable of allowing communication between the second conduit 2423 and the ambient air when the valve is placed in an open position. The valve 2439 is operably connected to a controller 2453 that is capable of controlling the opening and closing of the valve 2439 to regulate purging of the second conduit with ambient air to prevent blockages within the manifold 2415 and the first conduit 2419.

It should be noted that any fluid, including liquids or gases, could be used to accomplish the purging techniques described herein. While the driving force for the purging fluid is preferably the draw of reduced pressure at the tissue site, the fluid similarly could be delivered by a fluid delivery means similar to that discussed with reference to FIG. 9.

The administration of reduced pressure tissue treatment to a tissue site in accordance with the systems and methods described herein may be accomplished by applying a sufficient reduced pressure to the tissue site and then maintaining that sufficient reduced pressure over a selected period of time. Alternatively, the reduced pressure that is applied to the tissue site may be cyclic in nature. More specifically, the amount of reduced pressure applied may be varied according to a selected temporal cycle. Still another method of applying the reduced pressure may vary the amount of reduced pressure randomly. Similarly, the rate or volume of fluid delivered to the tissue site may be constant, cyclic, or random in nature. Fluid delivery, if cyclic, may occur during application of reduced pressure, or may occur during cyclic periods in which reduced pressure is not being applied. While the amount of reduced pressure applied to a tissue site will typically vary according to the pathology of the tissue site and the circumstances under which reduced pressure tissue treatment is administered, the reduced pressure will typically be between about −5 mm Hg and −500 mm Hg, but more preferably between about −5 mm Hg and −300 mm Hg.

While the systems and methods of the present invention have been described with reference to tissue growth and healing in human patients, it should be recognized that these systems and methods for applying reduced pressure tissue treatment can be used in any living organism in which it is desired to promote tissue growth or healing. Similarly, the systems and methods of the present invention may be applied to any tissue, including without limitation bone tissue, adipose tissue, muscle tissue, neural tissue, dermal tissue, vascular tissue, connective tissue, cartilage, tendons, or ligaments. While the healing of tissue may be one focus of applying reduced pressure tissue treatment as described herein, the application of reduced pressure tissue treatment, especially to tissues located beneath a patient's skin, may also be used to generate tissue growth in tissues that are not diseased, defective, or damaged. For example, it may be desired to use the percutaneous implantation techniques to apply reduced pressure tissue treatment to grow additional tissue at a tissue site that can then be harvested. The harvested tissue may be transplanted to another tissue site to replace diseased or damaged tissue, or alternatively the harvested tissue may be transplanted to another patient.

It is also important to note that the reduced pressure delivery apparatuses described herein may be used in conjunction with scaffold material to increase the growth and growth rate of new tissue. The scaffold material could be placed between the tissue site and the reduced pressure delivery apparatus, or the reduced pressure delivery apparatus could itself be made from bioresorbable material that serves as a scaffold to new tissue growth.

It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure delivery system for applying reduced pressure tissue treatment to a tissue site comprising:
    a manifold delivery tube having at least two lumens;
    a manifold having a plurality of flow channels, the manifold disposed within a first of the lumens of the manifold delivery tube; and
    a balloon having an inner space and being capable of assuming collapsed and expanded positions, the inner space being fluidly connected to a second of the lumens of the manifold delivery tube;
    wherein the manifold further comprises:
        a flexible wall surrounding a primary flow passage and adapted to be placed in proximity to the tissue site, the flexible wall including a plurality of apertures through the flexible wall and communicating with the primary flow passage;
        a blockage prevention member positioned within the primary flow passage;
        a first conduit having at least one outlet fluidly connected to the primary flow passage to deliver reduced pressure to the primary flow passage; and
        a second conduit having at least one outlet proximate the primary flow passage or the at least one outlet of the first conduit to purge at least one of the primary flow passage and the outlet of the first conduit with a gaseous fluid during the application of reduced pressure.

2. The reduced pressure delivery system according to claim 1, wherein the blockage prevention member is a plurality of projections disposed on an inner surface of the flexible wall and extending into the primary flow passage.

3. The reduced pressure delivery system according to claim 1, wherein the blockage prevention member is a cellular material positioned within the primary flow passage.

4. The reduced pressure delivery system according to claim 1, wherein the blockage prevention member is one or more ridges disposed on an inner surface of the flexible wall.

5. The reduced pressure delivery system according to claim 1, wherein the blockage prevention member is a divider.

6. The reduced pressure delivery system according to claim 5, wherein the divider bifurcates the primary flow passage.

7. The reduced pressure delivery system according to claim 1, wherein the apertures are selectively positioned around a circumference of the manifold.

8. The reduced pressure delivery system according to claim 1, wherein the apertures are configured to face a bone.

9. The reduced pressure delivery system according to claim 1, wherein the apertures are configured to face an overlying tissue.

10. The reduced pressure delivery system according to claim 1, wherein the apertures are configured to face a bone and an overlying tissue.

11. The reduced pressure delivery system according to claim 1, wherein the second conduit comprises more than one conduit.

12. The reduced pressure delivery system according to claim 1, wherein the manifold has an open end.

13. The reduced pressure delivery system according to claim 1, wherein the manifold has a closed end.

14. A manifold for applying reduced pressure tissue treatment to a tissue site comprising:
    a manifold delivery tube having at least a first lumen and a second lumen;
    a balloon having an inner space and being capable of assuming collapsed and expanded positions, the inner space being fluidly connected to the second lumen of the manifold delivery tube; and
    a manifold having a plurality of flow channels, the manifold disposed within the first lumen of the manifold delivery tube and further comprising:
        a flexible wall forming a primary flow passage and including a plurality of apertures extending through the flexible wall and communicating with the primary flow passage;
        a first conduit having at least one outlet fluidly connected to the primary flow passage to deliver reduced pressure to the primary flow passage; and
        a second conduit having an outlet proximate the primary flow passage or the at least one outlet of the first conduit to purge at least one of the primary flow passage and the outlet of the first conduit with a gaseous fluid during application of reduced pressure.

15. The manifold of claim 14, further comprising a blockage prevention member positioned within the primary flow passage.

16. The manifold of claim 15, wherein the blockage prevention member is a plurality of projections disposed on an inner surface of the flexible wall and extending into the primary flow passage.

17. The manifold of claim 15, wherein the blockage prevention member is a cellular material positioned within the primary flow passage.

18. The manifold of claim 14, wherein second conduit comprises more than one conduit.

19. The manifold of claim 14, wherein the manifold has an open end.

20. The manifold of claim 14, wherein the manifold has a closed end.

* * * * *